US005545545A

United States Patent [19]
Gengenbach et al.

[11] Patent Number: 5,545,545
[45] Date of Patent: Aug. 13, 1996

[54] LYSINE-INSENSITIVE MAIZE DIHYDRODIPICOLINIC ACID SYNTHASE

[75] Inventors: Burle G. Gengenbach; David A. Somers, both of St. Paul; Douglas C. Bittel, Cannon Falls; Jonathan M. Shaver, St. Paul, all of Minn.; Juantia M. Sellner, deceased, late of Earlville, Iowa, by James Sellner, Carlyn Sellner, executors

[73] Assignee: Regents of the University of Minnesota, Minneapolis, Minn.

[21] Appl. No.: 53,867

[22] Filed: Apr. 27, 1993

[51] Int. Cl.⁶ .......................... C12N 15/29; C12N 15/82; C07K 14/415; A01H 5/00
[52] U.S. Cl. ................... 435/172.3; 435/240.4; 530/376; 536/23.6; 800/205; 800/DIG. 56; 800/DIG. 70
[58] Field of Search ........................ 435/172.3, 240.4; 530/376; 536/23.6; 800/205

[56] References Cited

U.S. PATENT DOCUMENTS

| | | | |
|---|---|---|---|
| 5,066,595 | 11/1991 | Hubbard et al. | 435/240.45 |
| 5,082,993 | 1/1992 | Strissel et al. | 800/200 |
| 5,162,602 | 11/1992 | Somers et al. | 800/235 |

FOREIGN PATENT DOCUMENTS

| | | |
|---|---|---|
| 142924 | 5/1985 | European Pat. Off. . |
| 218571 | 4/1987 | European Pat. Off. . |
| 485970 | 5/1992 | European Pat. Off. . |
| 87/04181 | 7/1987 | WIPO . |
| 89/11789 | 12/1989 | WIPO . |

OTHER PUBLICATIONS

Shaul et al. 1992 The Plant Journal 2(2):203–209.
Perl et al 1992 Plant Molecular Biology 19:815–823.
P. P. Abel et al., "Delay of disease development in transgenic plants that express the tobacco mosaic virus coat protein gene", *Science*, 232, 738–743 (1986).
P. Arruda et al., "Regulation of aspartate kinase isoenzymes in barley mutants resistant to lysine plus threonine", *Plant Physiol.*, 76, 442–446 (1984).
J. P. Bourgin et al., 1982, in *Variability in Plants Regenerated from Tissue Culture*, Amino Acid–Resistant Plants from Tobacco Cells Selected in vitro, Earle and Demarly (eds.) pp. 163–174, Praeger, New York).
C. J. Boyes et al., "In vitro selection for tolerance to S–(2–Aminoethyl)–L–Cysteine and overproduction of lysine by embryogenic calli and regenerated plants of *Pennisetum americanum* (L.) K. Schum", *Plant Sci.*, 50, 195–203 (1987).
S. W. J. Bright et al., "Lysine metabolism in barley mutant resistant to S(2–aminoethyl)cysteine", *Planta*, 146, 692–633 (1979).
J. K. Bryan, 1980, in *The Biochemistry of Plants*, vol. 5, Synthesis of the Aspartate Family and Branched–Chain Amino Acids, Miflin (ed.), pp. 420–426.

A. Cattoir–Reynaerts et al., "Selection and characterization of carrot embryoid cultures resistant to inhibition by lysine plus threonine", *Biochem. Physiol. Pflanzen*, 178, 81–90 (1983).
L. Comai et al., "Expression in plants of a mutant *aroA* gene from *Salmonella typhimurium* confers tolerance to glyphosate", *Nature*, 317, 741–744 (1985).
M. De Block et al., "Engineering herbicide resistance in plants by expression of a detoxifying enzyme", *EMBO*, 6, 2513–2518 (1987).
D. A. Frisch et al., "Direct genetic selection of a maize cDNA for dihydrodipicolinate synthase in an *Escherichia coli* dapA–auxotroph", *Mol. Gen. Genet.*, 228, 287–293 (1991).
D. A. Frisch et al., "Isolation and characterization of dihydrodipicolinate synthase from Maize", *Plant Physiol.*, 96, 444–452 (1991).
B. G. Gengenbach et al., Agronomy Society Meeting abstract, Oct. 1990, "Molecular Genetics of Lysine Biosynthesis in *Zea mays*".
C. E. Green et al. "Potential selection system for mutants with increased lysine, threonine, and methionine in cereal crops", *Crop Sci.*, 14, 827–830 (1974).
G. W. Haughn et al., "Transformation with a mutant *Arabidopsis* acetolactate synthase gene renders tobacco resistant to sulfonylurea herbicides", *Mol. Gen. Genet.*, 211, 266–271 (1988).
K. A. Hibberd et al., "Selection and characterization of a feedback–insensitive tissue culture of maize", *Planta*, 148, 183–187 (1980).
K. A. Hibberd et al, "Inheritance and expression of lysine plus threonine resistance selected in maize tissue culture", *PNAS*, 79, 559–563 (1982).
E. Jacobsen, "Isolation, characterization and regeneration of an S–(2–aminoethyl)cysteine resistant cell line of dihaploid potato", *J. Plant Physiol.*, 123, 307–315 (1986).
E. T. Mertz et al., "Mutant gene that changes protein composition and increases lysine content of maize endosperm", *Science*, 145, 279 (1964).
L. Munck et al., "Gene for improved nutritional value in barley seed protein", *Science*, 168, 985–987 (1970).
I. Negrutiu et al., "Lysine overproducer mutants with an altered dihydrodipicolinate synthase from protoplast culture of *Nicotiana sylvestris* (Spegazzini and Comes)", *Theor. Appl. Genet.*, 68, 11–20 (1984).
R. S. Nelson et al., "Virus tolerance, plant growth, and field performance of transgenic tomato plants expressing coat protein from tobacco mosaic virus", *Bio/Technol.*, 6, 403–405 (1988).

(List continued on next page.)

*Primary Examiner*—Patricia R. Moody
*Attorney, Agent, or Firm*—Merchant, Gould, Smith, Edell, Welter & Schmidt

[57] ABSTRACT

A DNA sequence is provided which encodes an altered form of native *Zea mays* dihydrodipicolinic acid synthase (DHPS) which is substantially resistant to concentrations of L-lysine which inhibit the activity of native *Zea mays* DHPS, either in vitro or in transformed plant cells or whole plants.

27 Claims, 9 Drawing Sheets

OTHER PUBLICATIONS

O. E. Nelson et al., "Second mutant gene affecting the amino acid pattern of maize endosperm proteins", *Science*, 150, 1469–1470 (1965).

K. Sano et al., "Microbial production of L–lysine III. Production by mutants resistant to S–(2–aminoethyl)–L–cysteine", *J. Gen. Appl. Microbiol.*, 16, 373–391 (1970).

G. W. Schaeffer et al., "Increased lysine and seed storage in protein in rice plants recovered from calli selected with inhibitory levels of lysine plus threonine and S–(2–aminoethyl)cysteine", *Plant Physiol.*, 84, 509–515 (1987).

J. M. Sellner et al., "Selection of a cDNA expressing lysine–insensitive dihydrodipicolinate synthase activity", Maize Genetics Coop. Newsletter, Mar. 15, 1992 (Apr. 28, 1992 mailing date), p. 94.

D. M. Shah et al., "Engineering Herbicide Tolerance in Transgenic Plants", *Science*, 233, 478–481 (1986).

R. Singh et al., "High lysine mutant gene (hl) that improves protein quality and biological value of grain sorghum", *Crop Sci.*, 13, 535–539 (1973).

J. L. Taylor et al., "Optimizing the expression of chimeric genes in plant·cells", *Mol. Gen. Genet.*, 210, 572–577 (1987).

A. M. Tommey et al., "Molecular regulation of lysine biosynthesis in maize", *J. Cellular Biochem.*, supp. 15A (1991) 82.

M. Vacek et al., "Transgenic plants protected from insect attack", *Nature*, 328, 33–37 (1987).

R. M. Wallsgrove et al., "Spinach leaf dihydrodipicolinate synthase: partial purification and characterization", *Phytochem.*, 20, 2651–2655 (1981).

J. M. Widholm, "Selection and characterization of cultured carrot and tobacco cells resistant to lysine, methionione, and proline analogs", *Can. J. Bot.*, 54, 1523–1529 (1976).

FIG. 3-1

```
     -108 ATGACCATGATTACGCCAAGCTTGCATGCC
          TGCAGGTCGACTCTAGAGGATCCCCGGGTACCGAGCTCG
          AATTCCACGACCACGCCCTCCGTGCTCCAGCCATTCCCC

1   ATG ATT TCG CCG ACG AAT CTC CTC CCG GCG
       MET Ile Ser Pro Thr Asn Leu Leu Pro Ala

31   CGG AAG ATC ACC CCT GTC TCA AAT GGC GGC
       Arg Lys Ile Thr Pro Val Ser Asn Gly Gly

61   GCA GCG ACG GCG AGC CCC TCT TCT CCC TCG
       Ala Ala Thr Ala Ser Pro Ser Ser Pro Ser

91   GTG GCC GCA CGG CCA CGG CGA CTC CCT TCA
       Val Ala Ala Arg Pro Arg Arg Leu Pro Ser

121   GGC CTC CAA TCT GTG ACT GGT AGA GGG AAG
       Gly Leu Gln Ser Val Thr Gly Arg Gly Lys

151   GTT TCC TTG GCA GCC ATC ACT CTA GAT GAT
       Val Ser Leu Ala Ala Ile Thr Leu Asp Asp

181   TAC CTT CCA ATG CGA AGC ACT GAA GTG AAG
       Tyr Leu Pro Met Arg Ser Thr Glu Val Lys

211   AAC CGG ACA TCA ACA GAT GAC ATC ACA AGG
       Asn Arg Thr Ser Thr Asp Asp Ile Thr Arg

241   CTG AGA CTA ATC ACA GCA GTT AAA ACC CCC
       Leu Arg Leu Ile Thr Ala Val Lys Thr Pro

271   TAT TTG CCA GAT GGG AGG TTC GAT CTG GAA
       Tyr Leu Pro Asp Gly Arg Phe Asp Leu Glu

301   GCA TAT GAT TCT CTC ATA AAC ATG CAG ATA
       Ala Tyr Asp Ser Leu Ile Asn Met Gln Ile

331   GAG GGT GGT GCC GAA GGC GTA ATA GTT GGA
       Glu Gly Gly Ala Glu Gly Val Ile Val Gly

361   GGA ACA ACA GGA GAG GGT CAC CTC ATG AGC
       Gly Thr Thr Gly Glu Gly His Leu Met Ser
```

FIG. 3-2

```
391    TGG GAC GAA CAT ATC ATG CTC ATT GGG CAC
       Trp Asp Glu His Ile Met Leu Ile Gly His

421    ACA GTG AAC TGC TTT GGC TCT AGA ATC AAA
       Thr Val Asn Cys Phe Gly Ser Arg Ile Lys

451    GTG ATA GGC AAC ACA GGA AGC AAC TCA ACC
       Val Ile Gly Asn Thr Gly Ser Asn Ser Thr

481    AGA GAA GCC GTC CAC GCA ACA GAA CAG GGA
       Arg Glu Ala Val His Ala Thr Glu Gln Gly

511    TTT GCT GTT GGC ATG CAT GCG GCT CTC CAC
       Phe Ala Val Gly Met His Ala Ala Leu His

541    ATC AAT CCT TAC TAC GGG AAG ACC TCA GCT
       Ile Asn Pro Tyr Tyr Gly Lys Thr Ser Ala

571    GAA GGA ATG ATC TCT CAT TTC GAG GCT GTC
       Glu Gly Met Ile Ser His Phe Glu Ala Val

601    CTC CCG ATG GGT CCG ACC ATC ATC TAC AAC
       Leu Pro Met Gly Pro Thr Ile Ile Tyr Asn

631    GTG CCA TCC AGG AGC GCC CAG GAC ATC CCC
       Val Pro Ser Arg Ser Ala Gln Asp Ile Pro

661    CCT GAA GTT ATT CTA GCG ATT TCT GGC TAC
       Pro Glu Val Ile Leu Ala Ile Ser Gly Tyr

691    ACA AAC ATG GCG GGT GTC AAG GAA TGT GTT
       Thr Asn Met Ala Gly Val Lys Glu Cys Val

721    GGG CAC GAG AGG GTT AAG CAC TAC GCT GAC
       Gly His Glu Arg Val Lys His Tyr Ala Asp

751    AAA GGC ATA ACA ATT TGG AGC GGT AAC GAC
       Lys Gly Ile Thr Ile Trp Ser Gly Asn Asp

781    GAC GAG TGC CAC GAT TCT AAG TGG AAA CAT
       Asp Glu Cys His Asp Ser Lys Trp Lys His

811    GGC GCT ACT GGG GTC ATT TCC GTT ACC AGC
       Gly Ala Thr Gly Val Ile Ser Val Thr Ser
```

FIG. 3-3

```
841   AAC CTT GTT CCC GGG CTC ATG CAC AGC CTC
      Asn Leu Val Pro Gly Leu Met His Ser Leu

871   ATG TAC AAA GGC GAG AAC GCC ACG CTG AAC
      Met Tyr Lys Gly Glu Asn Ala Thr Leu Asn

901   GAG AAG CTG TCG CCC CTG ATG AAA TGG CTG
      Glu Lys Leu Ser Pro Leu Met Lys Trp Leu

931   TTC TGC CAG CCA AAT CCT ATT GCC CTC AAC
      Phe Cys Gln Pro Asn Pro Ile Ala Leu Asn

961   ACT GCT CTG GCT CAG CTC GGC GTG GCA AGG
      Thr Ala Leu Ala Gln Leu Gly Val Ala Arg

991   CCT GTC TTC AGA CTG CCG TAC GTT CCG CTC
      Pro Val Phe Arg Leu Pro Tyr Val Pro Leu

1021  CCT CTT GAA AAG AGG GCC GAG TTC GTC CGG
      Pro Leu Glu Lys Arg Ala Glu Phe Val Arg

1051  ATT GTT GAG TCA ATT GGA CGG GAA AAT TTC
      Ile Val Glu Ser Ile Gly Arg Glu Asn Phe

1081  GTG GGG CAG AAG GAG GCC CAG GTT CTA GAT
      Val Gly Gln Lys Glu Ala Gln Val Leu Asp

1111  GAT GAC GAT TTC GTG TTG ATC AGT AGG TAC
      Asp Asp Asp Phe Val Leu Ile Ser Arg Tyr

1141  TAG GAAAATGAGTTTGCTAGTCTATGTATCTTGGCGAA
      TAAACTAGTAGTTTGTACCTTGCGTTCAGACTTCGTTCT
      GTTGTTCATCAGTCGTTGGTTTCGTCTATCTATTTATTA
      ATTGCCTACTTTGGCCGCATTGTATAATGGATATGTATC
      GCGTTTATAGTTTTTTACGTGAATTGACCTAGGGACAAG
      GAAAAAATGGTCACTTCTTTTTTGGCT
```

FIG. 5-1

```
     -108 ATGACCATGATTACGCCAAGCTTGCATGCC
          TGCAGGTCGACTCTAGAGGATCCCCGGGTACCGAGCTCG
          AATTCCACGACCACGCCCTCCGTGCTCCAGCCATTCCCC
```

|     |     |     |     |     |     |     |     |     |     |
|-----|-----|-----|-----|-----|-----|-----|-----|-----|-----|
| 1   | ATG | ATT | TCG | CCG | ACG | AAT | CTC | CTC | CCG GCG |
|     | MET | Ile | Ser | Pro | Thr | Asn | Leu | Leu | Pro Ala |
| 31  | CGG | AAG | ATC | ACC | CCT | GTC | TCA | AAT | GGC GGC |
|     | Arg | Lys | Ile | Thr | Pro | Val | Ser | Asn | Gly Gly |
| 61  | GCA | GCG | ACG | GCG | AGC | CCC | TCT | TCT | CCC TCG |
|     | Ala | Ala | Thr | Ala | Ser | Pro | Ser | Ser | Pro Ser |
| 91  | GTG | GCC | GCA | CGG | CCA | CGG | CGA | CTC | CCT TCA |
|     | Val | Ala | Ala | Arg | Pro | Arg | Arg | Leu | Pro Ser |
| 121 | GGC | CTC | CAA | TCT | GTG | ACT | GGT | AGA | GGG AAG |
|     | Gly | Leu | Gln | Ser | Val | Thr | Gly | Arg | Gly Lys |
| 151 | GTT | TCC | TTG | GCA | GCC | ATC | ACT | CTA | GAT GAT |
|     | Val | Ser | Leu | Ala | Ala | Ile | Thr | Leu | Asp Asp |
| 181 | TAC | CTT | CCA | ATG | CGA | AGC | ACT | GAA | GTG AAG |
|     | Tyr | Leu | Pro | Met | Arg | Ser | Thr | Glu | Val Lys |
| 211 | AAC | CGG | ACA | TCA | ACA | GAT | GAC | ATC | ACA AGG |
|     | Asn | Arg | Thr | Ser | Thr | Asp | Asp | Ile | Thr Arg |
| 241 | CTG | AGA | CTA | ATC | ACA | GCA | GTT | AAA | ACC CCC |
|     | Leu | Arg | Leu | Ile | Thr | Ala | Val | Lys | Thr Pro |
| 271 | TAT | TTG | CCA | GAT | GGG | AGG | TTC | GAT | CTG GAA |
|     | Tyr | Leu | Pro | Asp | Gly | Arg | Phe | Asp | Leu Glu |
| 301 | GCA | TAT | GAT | TCT | CTC | ATA | AAC | ATG | CAG ATA |
|     | Ala | Tyr | Asp | Ser | Leu | Ile | Asn | Met | Gln Ile |
| 331 | GAG | GGT | GGT | GCC | GAA | GGC | GTA | ATA | GTT GGA |
|     | Glu | Gly | Gly | Ala | Glu | Gly | Val | Ile | Val Gly |
| 361 | GGA | ACA | ACA | GGA | GAG | GGT | CAC | CTC | ATG AGC |
|     | Gly | Thr | Thr | Gly | Glu | Gly | His | Leu | Met Ser |

FIG. 5-2

```
391    TGG GAC GAA CAT ATC ATG CTC ATT GGG CAC
       Trp Asp Glu His Ile Met Leu Ile Gly His

421    ACA GTG AAC TGC TTT GGC TCT AGA ATC AAA
       Thr Val Asn Cys Phe Gly Ser Arg Ile Lys

451    GTG ATA GGC AAC ACA GGA AGC AAC TCA ACC
       Val Ile Gly Asn Thr Gly Ser Asn Ser Thr

481    AGA GAA GCC GTC CAC GTA ACA GAA CAG GGA
       Arg Glu Ala Val His Val Thr Glu Gln Gly

511    TTT GCT GTT GGC ATG CAT GCG GCT CTC CAC
       Phe Ala Val Gly Met His Ala Ala Leu His

541    ATC AAT CCT TAC TAC GGG AAG ACC TCA GCT
       Ile Asn Pro Tyr Tyr Gly Lys Thr Ser Ala

571    GAA GGA ATG ATC TCT CAT TTC GAG GCT GTC
       Glu Gly Met Ile Ser His Phe Glu Ala Val

601    CTC CCG ATG GGT CCG ACC ATC ATC TAC AAC
       Leu Pro Met Gly Pro Thr Ile Ile Tyr Asn

631    GTG CCA TCC AGG AGC GCC CAG GAC ATC CCC
       Val Pro Ser Arg Ser Ala Gln Asp Ile Pro

661    CCT GAA GTT ATT CTA GCG ATT TCT GGC TAC
       Pro Glu Val Ile Leu Ala Ile Ser Gly Tyr

691    ACA AAC ATG GCG GGT GTC AAG GAA TGT GTT
       Thr Asn Met Ala Gly Val Lys Glu Cys Val

721    GGG CAC GAG AGG GTT AAG CAC TAC GCT GAC
       Gly His Glu Arg Val Lys His Tyr Ala Asp

751    AAA GGC ATA ACA ATT TGG AGC GGT AAC GAC
       Lys Gly Ile Thr Ile Trp Ser Gly Asn Asp

781    GAC GAG TGC CAC GAT TCT AAG TGG AAA CAT
       Asp Glu Cys His Asp Ser Lys Trp Lys His

811    GGC GCT ACT GGG GTC ATT TCC GTT ACC AGC
       Gly Ala Thr Gly Val Ile Ser Val Thr Ser
```

FIG. 5-3

```
841   AAC CTT GTT CCC GGG CTC ATG CAC AGC CTC
      Asn Leu Val Pro Gly Leu Met His Ser Leu

871   ATG TAC AAA GGC GAG AAC GCC ACG CTG AAC
      Met Tyr Lys Gly Glu Asn Ala Thr Leu Asn

901   GAG AAG CTG TCG CCC CTG ATG AAA TGG CTG
      Glu Lys Leu Ser Pro Leu Met Lys Trp Leu

931   TTC TGC CAG CCA AAT CCT ATT GCC CTC AAC
      Phe Cys Gln Pro Asn Pro Ile Ala Leu Asn

961   ACT GCT CTG GCT CAG CTC GGC GTG GCA AGG
      Thr Ala Leu Ala Gln Leu Gly Val Ala Arg

991   CCT GTC TTC AGA CTG CCG TAC GTT CCG CTC
      Pro Val Phe Arg Leu Pro Tyr Val Pro Leu

1021  CCT CTT GAA AAG AGG GCC GAG TTC GTC CGG
      Pro Leu Glu Lys Arg Ala Glu Phe Val Arg

1051  ATT GTT GAG TCA ATT GGA CGG GAA AAT TTC
      Ile Val Glu Ser Ile Gly Arg Glu Asn Phe

1081  GTG GGG CAG AAG GAG GCC CAG GTT CTA GAT
      Val Gly Gln Lys Glu Ala Gln Val Leu Asp

1111  GAT GAC GAT TTC GTG TTG ATC AGT AGG TAC
      Asp Asp Asp Phe Val Leu Ile Ser Arg Tyr

1141  TAG GAAAATGAGTTTGCTAGTCTATGTATCTTGGCGAA
      TAAACTAGTAGTTTGTACCTTGCGTTCAGACTTCGTTCT
      GTTGTTCATCAGTCGTTGGTTTCGTCTATCTATTTATTA
      ATTGCCTACTTTGGCCGCATTGTATAATGGATATGTATC
      GCGTTTATAGTTTTTTACGTGAATTGACCTAGGGACAAG
      GAAAAAATGGTCACTTCTTTTTTGGCT
```

LYSINE-INSENSITIVE MAIZE DIHYDRODIPICOLINIC ACID SYNTHASE

GOVERNMENT SUPPORT

The present invention was made with government support under USDA 90-34190-5207 awarded by the Midwest Plant Biotechnology Consortium. The government has certain rights in the invention.

SUMMARY OF THE INVENTION

Recent advances in gene transfer technology have opened up new possibilities for introducing desirable traits into plants. A number of such genes have been introduced, in order to confer upon the host plant some measure of protection against environmental stresses. Examples include genes conferring tolerance to chemical herbicides such as glyphosate (Comai, *Nature,* 317, 741–744 (1985) and Shah, *Science,* 233, 478–481 (1986)), phosphinothricin (De Block, *EMBO,* 6, 2513–2518 (1987)), bromoxynil (Stalker, 1987, International Patent Application No. PCT/US 87/00044), and sulfonylureas (Haughn, *Mol. Gen. Genet.,* 211, 266–271 (1988)). Transgenic plants have also been engineered to resist certain insect pests (Adang, 1985, published European Patent Application No. 142,924 and Vacek, *Nature,* 328, 33–37 (1987)), fungal diseases (Taylor, *Mol. Gen. Genet.,* 210, 572–577 (1987)), and viral diseases (Abel, *Science,* 232, 738–743 (1986) and Nelson, *Bio/Technol.,* 6, 403–405 (1988)).

Another area of interest is the design of plants, especially crop plants, with added value traits. An example of such a trait is improved nutritional quality in food crops. Lysine, an amino acid essential in the diet of humans and monogastric animals, is among the three most limiting nutrients in most of the cereal crops. Consequently, grain-based diets, such as those based on corn, barley, wheat, rice, maize, millet, sorghum, and the like, must be supplemented with more expensive synthetic lysine or with lysine-containing oilseed protein meals. Increasing the lysine content of these grains or of any of the feed component crops would result in significant added value. To date, attempts to elevate lysine levels in plants have relied on conventional breeding methods. More recently, mutagenesis and cell culture technology, as well as recombinant DNA and gene transfer methodologies, have also been applied to introduce altered or non-native genes into maize.

Naturally occurring high lysine mutants of maize (Mertz, *Science,* 145, 279 (1964) and Nelson, *Science,* 150, 1469–1470 (1965)), barley (Munck, *Science,* 168, 985–987 (1970)), and grain sorghum (Singh et al., *Crop Sci.,* 13, 535–539 (1973)) have been identified. In each case, the improved lysine content results not from increased free lysine production, but from shifts in the overall protein profile of the grain: the reduced levels of lysine-deficient endosperm proteins (prolamines) are complemented by elevated levels of more lysine-rich proteins (albumins, globulins and glutelins). While nutritionally superior, these mutants are associated with reduced yields and poor grain quality, limiting their agronomic usefulness.

An alternative approach used to improve nutritional quality has been in vitro selection for biochemical variants having elevated free lysine pools. Lysine is a member of the "aspartate family" of amino acids in higher plants and microorganisms (see FIG. 1). As such, the regulation of its biosynthesis is intimately connected to that of the other members of the family: threonine, methionine and isoleucine. Regulation of metabolite flow appears to be chiefly through endproduct feedback inhibition at key enzymatic steps. The first of these steps, the phosphorylation of aspartate catalyzed by aspartate kinase (AK), is common to all four endproducts. A second site of regulation is at the branch-point reaction: the condensation of pyruvate with aspartyl semialdehyde to form dihydrodipicolinic acid. This reaction is the first one unique to the biosynthesis of lysine and is catalyzed by dihydrodipicolinic acid synthase (DHPS), an enzyme shown to be strongly feedback-inhibited by lysine in plants where it has been examined (Wallsgrove et al., *Phytochem.,* 20, 2651–2655 (1981), and Kumpaisal, *Plant Physiol.,* 85, 145–151 (1987)).

There is evidence to suggest the existence of more than one form of AK (Miflin, 1980, in *The Biochemistry of Plants,* vol. 5, *Amino Acids and Derivatives,* Stumpf and Conn (eds.) pp. 420–426, Academic Press). One form is sensitive to inhibition by threonine, the other to inhibition by lysine. The growth of plant cell cultures is inhibited in the presence of equimolar amounts of lysine plus threonine. This inhibition may be reversed by the addition of methionine or homoserine (which may be readily converted to methionine) (Green et al., *Crop Sci.,* 14, 827–830 (1974)). Hibberd (*Planta,* 148, 183–187 (1980)) selected stable lines of maize callus that were resistant to this growth inhibition. These lines overproduced threonine (6–9 fold) and to a lesser extent, methionine, lysine and isoleucine (2–4 fold). There was evidence that a lysine-tolerant AK was responsible for the changes observed. In the lines that were regenerated to whole, fertile plants, the overproduction was a stable, heritable trait (Hibberd et al, *PNAS,* 79, 559–563 (1982)). Similar selections have been carried out on tobacco (Bourgin, 1982, in *Variability in Plants Regenerated from Tissue Culture,* Earle and Demarly (eds.) pp. 163–174, Praeger, New York), barley (Arruda, *Plant Physiol.,* 76, 442–446 (1984)), and carrot (Cattoir-Reynaerts, *Biochem. Physiol. Pfanzen,* 178, 81–90 (1983)).

Lysine analogs, in particular S(2-aminoethyl)cysteine (AEC) have also been used either alone or in conjunction with lysine plus threonine selections in attempts to isolate lysine-overproducing mutants. Sano et al. (*J. Gen. Appl. Microbiol.,* 16, 373–391 (1970)) were able to isolate high lysine bacterial mutants using AEC selection and AEC was proposed to act as a false feedback inhibitor of AK or DHPS or both. Attempts to isolate similar mutants in plants have had mixed results. Widholm (*Can. J. Bot.,* 54, 1523–1529 (1976)) mutagenized tobacco suspension cells and selected AEC-resistant cell lines that overproduced lysine by tenfold. Pearl millet mutants were isolated that overproduced lysine by 5–7 fold (Boyes et al., *Plant Sci.,* 50, 195–203 (1987)). Bright (*Planta,* 146, 629–633 (1979)) selected AEC-resistant barley lines that did not accumulate lysine in the absence of AEC and were shown to be AEC uptake mutants. There was also evidence that AEC exerted its inhibitory effects by being incorporated into proteins rather than by interfering with lysine biosynthesis. Schaeffer et al. (*Plant Physiol.,* 84, 509–515 (1987)) applied sequential AEC and lysine plus threonine selections to obtain rice mutants that had 14% higher lysine in seed storage proteins, but not higher free lysine. An AEC-resistant potato culture was selected by Jacobsen (*J. Plant Physiol.,* 123, 307–315 (1986)). This mutant had higher overall amino acid levels than control cultures but this was not due to overproduction of lysine, threonine or methionine. Negrutiu (*Theor. Appl. Genet.,* 68, 11–20 (1984)) subjected tobacco protoplasts to mutagenesis followed by AEC selection. Two resistant cell lines were obtained that overproduced lysine by 10–30 fold.

Biochemical and genetic analysis revealed a feedback-insensitive DHPS synthase. The trait was inherited as a single dominant gene.

More recently, both G. Galili et al. (published European Patent Application 485,970) and K. Glassman et al. (PCT/ US 89/01309) have reported the *A. tumefaciens*-mediated transformation of tobacco and potato plants to introduce the *E. coli* dap A gene linked to a chloroplast transit peptide. The *E. coli* dap A gene encodes a form of DHPS which is more resistant to feedback inhibition by L-lysine than known plant DHPS. These groups were able to demonstrate the overproduction of free lysine in leaves of the transgenic tobacco and potato plants. However, these applications do not disclose the transformation of maize with the *E. coli* dap A gene constructs.

Considering the relative inability of conventional breeding and tissue culture technology to readily obtain plants accumulating significantly higher levels of lysine in maize, a continuing need exists to apply recombinant DNA and gene transfer technology to produce such plants.

SUMMARY OF THE INVENTION

The present invention provides an isolated recombinant DNA sequence encoding an altered *Zea mays* (maize) dihydrodipicolinic acid synthase (DHPS) which is substantially resistant to feedback inhibition by L-lysine. For example, a preferred embodiment of the present invention provides an isolated altered *Zea mays* DHPS, shown in SEQ ID NO. 2, which is more than 400 times less sensitive to lysine than the corresponding autologous or "native" *Zea mays* DHPS. A preferred recombinant DNA sequence of the invention, shown in SEQ ID NO. 1, expresses DHPS activity in *E. coli* transformants that is not inhibited by 1000 μM lysine, while the corresponding wildtype maize DHPS activity is more than 90% inhibited at 100 μM.

The *Zea mays* DHPS of the invention has been "altered" by replacement of one or more, preferably 1–5 of the peptidyl (or "amino acid") residues of a "native" or "endogenous" *Zea mays* DHPS, with peptidyl residues that enhance the ability of the altered enzyme to resist inhibition, e.g., by decreased binding with L-lysine, either in vitro or in transgenic plant cells. Although, as discussed hereinbelow, an effectively altered *Zea mays* DHPS can be prepared by in vitro mutations of native *Zea mays* DNA encoding DHPS, once an altered DHPS has been identified, it can be prepared synthetically, as by solid-phase peptide synthesis. Also, a mutated *Zea mays* DNA sequence encoding lysine-resistant DHPS can be amplified and further mutated by site-directed mutagenesis. Thereby, other sequence alterations, derivatives and subunits can be readily obtained, as disclosed hereinbelow. The reference to the altered DHPS as *"Zea mays"* or "maize" DHPS is intended to mean that the amino acid sequence of the DHPS (or the DNA sequence of the gene encoding it) that is altered, or modified, is derived either directly (as by cloning from a maize cDNA library) or indirectly, as by chemical synthesis, from a DHPS, or a gene encoding it, which occurs as a "native" sequence in the genome of *Zea mays*. As discussed hereinbelow, the maize genome may encode several different forms of DHPS, and each can provide the basis for the altered DHPS of the invention. The altered *Zea mays* DHPS will preferably comprise at least about 90% sequence homology with the corresponding unaltered native DHPS, most preferably about 95% sequence homology, i.e., 97–99% homology. Preferably, the altered *Zea mays* DHPS will comprise about 1–5 amino acid substitutions within the region of residues 100–125.

The present invention further provides a method of substantially increasing the level of free L-lysine in a plant, preferably a monocot, most preferably a *Zea mays* plant, comprising: (a) introducing a recombinant DNA sequence into the cells of a plant tissue source, and (b) expressing the recombinant DNA sequence in said cells, wherein said recombinant DNA sequence comprises a first DNA sequence which encodes an altered *Zea mays* dihydrodipicolinic acid synthase (DHPS) which is substantially resistant to feedback inhibition by endogenously produced free L-lysine. In the practice of the present method, the recombinant DNA sequence further comprises a second DNA sequence which is attached to the 5'-terminus of the altered DHPS DNA sequence, and which encodes a chloroplast transit peptide (CTP), preferably a *Zea mays* CTP. The CTP localizes the DHPS in the chloroplasts of said cells, where it can act to enhance the biosynthesis of free L-lysine.

Therefore, the present method also provides transgenic plant cells which have been stably transformed by the introduction of a recombinant DNA sequence which expresses an altered form of *Zea mays* DHPS which is substantially resistant to feedback inhibition by endogenous lysine. Since techniques are known by which totipotent cells from a number of *Zea mays* tissue sources can be regenerated into whole *Zea mays* plants, the present method also provides a transgenic *Zea mays* plant which produces free L-lysine by a biosynthetic pathway employing the altered maize DHPS, wherein the altered maize DHPS is the product of an introduced recombinant DNA sequence, and is substantially resistant to feedback-inhibition by endogenously produced lysine. Other plant cells and plants which can be produced by the present method include those of the other graminaceous species, such as those enumerated hereinabove. The edible parts of such transformed plants can have free L-lysine levels which are at least about 50 times higher than the lysine levels in an untransformed plant of the same species or variety.

The recombinant DNA sequence employed to transform the plant cells preferably comprises two or more linked, preselected structural genes. Such a DNA sequence can be referred to as a chimeric-gene expression cassette or construct, wherein a first DNA sequence encodes the altered *Zea mays* DHPS or an enzymatically functional fragment thereof which is substantially resistant to feedback inhibition by lysine, and a second DNA sequence encodes an amino-terminal chloroplast transit sequence (CTS). The DHPS-encoding sequence or a bioactive fragment thereof, is joined in correct reading frame at its 5'-terminus to the CTS gene. The structural genes are preferably also under the transcriptional and translational control of regulatory regions which are functional in the target plant cells. For example, the present chimeric recombinant DNA sequences can include plant promoters of various kinds, derived from both mono- and dicotyledonous plants; both non-tissue-specific and tissue-specific promoters.

Also, the expression cassette preferably further comprises a selectable marker gene or a reporter gene. A selectable marker gene encodes a function that is selectable in plant cells, such as drug or herbicide resistance, so that the transformed cells, and the plants derived therefrom, can be readily identified, and isolated from untransformed cells in a population which includes both.

A further embodiment of the present invention comprises an expression vector, such as a plasmid or phage, which incorporates the present chimeric expression cassette, wherein said plasmid is capable of replication in a bacterium such as *E. coli*. The recombinant DNA sequence can be introduced into the genome of bacterial or plant cells in vitro as "naked" DNA by methods such as electroporation, microinjection, microprojectile bombardment or via liposome encapsulation. Also, a plasmid incorporating the present recombinant DNA sequence can be introduced into the genome of dicot plant cells by *A. tumefaciens*-mediated transformation.

As used herein with respect to the recombinant DNA sequence which has been introduced into plant cells, the term "expresses" means that the gene is stably incorporated into the genome of the cells, so that the product encoded by the gene, i.e., an enzyme such as DHPS, is produced in a functional form within the cells. For example, a functional form of DHPS catalyzes a step in the endogenous biosynthesis of lysine.

As used herein with respect to the feedback inhibition of DHPS by endogenous lysine, the term "substantially resistant" means that the DHPS remains functional in the presence of endogenous lysine to the extent that the plant accumulates lysine substantially in excess of that accumulated by a plant of the same species which does not synthesize DHPS which is so resistant. For example, novel plants resulting from the present method contain extractable lysine levels at least about ten times, and preferably, at least about 50 times, e.g., about 50–250 times higher than plants of the same species which contain only native DHPS. However, the ability of the altered *Zea mays* DHPS to resist inhibition by lysine can also be evaluated in vitro and compared to the feedback inhibition exhibited by native *Zea mays* DHPS ($I_{50}$=25 µM lysine). Thus, an altered maize DHPS is substantially resistant to inhibition by lysine if it exhibits an $I_{50}$ at least 100× and preferably at least 500× that of the corresponding native *Zea mays* DHPS.

Furthermore, free lysine is not present in levels which are toxic to the particular plant species which has been altered. Also, plant cells or plants which are referred to as "transformed" or "transgenic" have the recombinant DNA sequence stably, functionally and inheritably integrated into their genome, so that the genome is augmented by said DNA sequence.

BRIEF DESCRIPTION OF THE DRAWINGS

FIG. 3 depicts the nucleotide and amino acid sequence for maize DHPS cDNA clone pZM DHPS5B (EMBL Data Bank accession number X52850) ATCC Accession NO. 69293 (SEQ ID No. 6). The 5' end of the cDNA begins at −39, the proposed translation initiation site is shown at +1 and the mature DHPS protein sequence begins at +163 (SEQ ID No. 7). The sequence of the transit peptide (+1 to 162) is underlined.

FIG. 5 depicts the nucleotide and amino acid sequence for maize DHPS cDNA clone pZM DHPS-M1 (SEQ ID No. 3). The 5' end of the cDNA begins at −39, the proposed translation initiation site is shown at +1, and the sequence of the transit peptide (+1 to 162) is underlined (SEQ ID No. 4). The single base change mutation at position #497 (C->T) causes a substitution of the amino acid valine for the alanine found in the wildtype DHPS cDNA pZM DHPS5B.

DETAILED DESCRIPTION OF THE INVENTION

Figure 1:
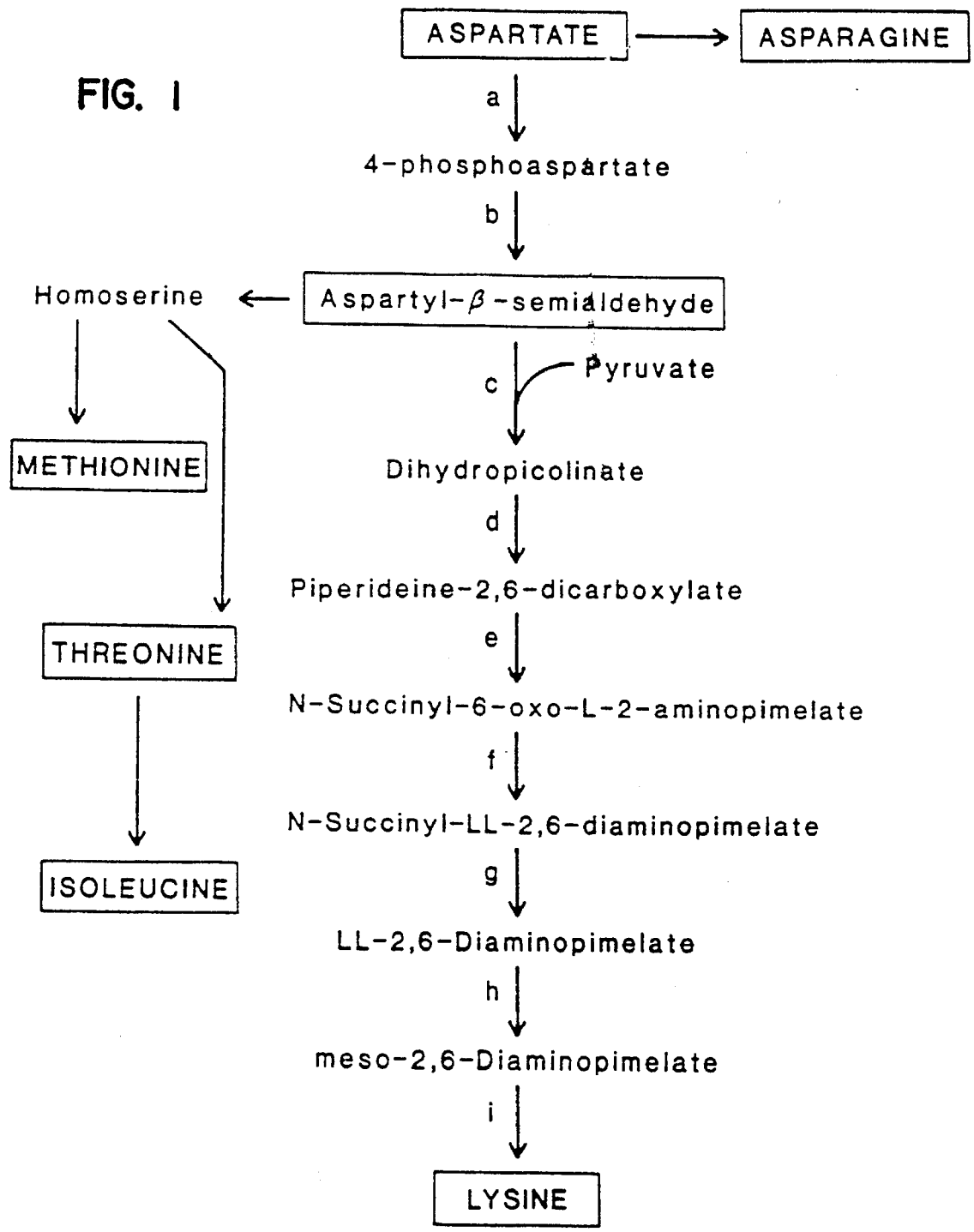
FIG. 1 is a schematic depiction of the lysine biosynthetic pathway wherein the following letters indicate the following enzymes: a—aspartate kinase; b—aspartylsemialdehyde dehydrogenase; c—dihydrodipicolinic acid synthase; d—dihydrodipicolinic acid reductase; e—succinyloxoaminopimelate synthase; f—succinyldiaminopimelate amino transferase; g—succinyldiaminopimelate desuccinylase; h-diaminopimelate; and i—meso-diaminopimelate decarboxylase.

The present invention relates to a novel method for obtaining transgenic plants, particularly monocot plants such as the grains, that produce elevated levels of free lysine. The overproduction results from the introduction and expression of a recombinant DNA sequence encoding an altered *Zea mays* dihydrodipicolinic acid (DHP) synthase, the branch-point enzyme in the biosynthesis of lysine in both plants and bacteria. Native plant DHP synthase is generally highly sensitive to feedback inhibition by L-lysine ($I_{50}$=25 µM) and constitutes a key site of regulation of the pathway. By contrast, the altered maize DHPS of the invention is active in the presence of at least 100-fold higher levels of L-lysine in vitro.

In order for the introduction of any gene encoding a lysine-tolerant DHPS to result in the accumulation of higher levels of free lysine in a plant, a long and complex chain of events must occur. In the first place, it is preferred to modify the cloned, mutated *Zea mays* DHPS gene in vitro to include or add regulatory signals required for gene expression in the target plant cells. For example, the CTP-encoding sequence and the DHPS sequence may be placed under the control of a "strong promoter" for expression in *Zea mays*, preferably positioned upstream from an intron which promotes expression of the structural genes in maize.

In order to alter the biosynthesis of lysine, the altered maize DHPS gene must be introduced into the plant cells and these transformed cells identified. The gene must also be stably incorporated into the plant cell genome. The transcriptional signals of the altered gene must be retained, recognized by and be functional in the plant cells. That is, the altered gene must be transcribed into messenger RNA, and the mRNA must be stable in the plant nucleus and be transported intact to the cytoplasm for translation. The gene must have appropriate translational signals to be recognized and properly translated by plant cell ribosomes. The nonnative polypeptide gene product must escape proteolytic attack in the cytoplasm and be able to assume a three-dimensional conformation that will confer enzymic activity. The DHPS must further be able to function in the biosynthesis of lysine; that is, it must be localized near the native plant enzymes catalyzing the flanking steps in biosynthesis (presumably in the chloroplast) in order to obtain the required substrates (aspartyl semialdehyde and pyruvate) and to pass on the appropriate product (dihydrodipicolinic acid).

Even if all these conditions are met, successful overproduction of lysine is not a predictable event. There must be no other control mechanism compensating for the reduced regulation at the DHPS synthase step. This means not only no other inhibition of biosynthesis, but also no mechanism to increase the rate of breakdown of the accumulated lysine. Lysine must be also overproduced at levels which are not toxic to host cells in vitro or to the transformed plant. Finally, the introduced trait must be stable and heritable in order to permit commercial development and use.

Since the present lysine-resistant DHPS is derived from native lysine-sensitive DHPS, it was first necessary to isolate and characterize the *Zea mays* DHPS-encoding gene and its gene product. Isolation methodologies include immunological screening of polypeptides expressed from gene libraries; screening a genomic library for hybridization to a radiolabelled oligonucleotide probe, PCR location and amplification of DHPS-encoding sequences using primers based on known DHPS genes, and the like.

The oligonucleotide probe may be synthesized based on sequences derived from genes of other species or from reverse translation of the polypeptide sequence of an isolated DHPS subunit. Once the sequence of the native DHPS gene is known, oligonucleotides complementary to the 3'- and 5'-ends of the strands can be synthesized and used in the polymerase chain reaction (PCR) to identify and amplify other maize or monocot DNA sequences encoding DHPS.

The isolated gene is characterized using standard recombinant DNA manipulations and molecular analyses. Such techniques are well known to those in the art and are outlined in Maniatis et al., *Molecular Cloning: A Laboratory Manual*, Cold Spring Harbor Laboratory, New York (1982) (hereinafter *"Molecular Cloning"*). Typically, the DNA fragment carrying the DHPS gene is reduced to the smallest functional fragment possible; that is, extraneous DNA flanking the gene is removed by methods such as Bal31 digestion, deletion of a known restriction endonuclease fragment, and the like, to obtain the smallest DNA fragment that will, for example, still complement the DHPS mutant. This fragment is usually less than three kilobases, more commonly, about one kilobase. The nucleotide sequence of this DNA fragment may then be determined by any of several conventional methods. The open reading frame (coding sequence), the putative RNA polymerase binding site (promoter), the chloroplast transit peptide-encoding region, ribosomal binding site, and the transcriptional termination signal sequence may then be identified. The transcriptional initiation site may be determined by techniques such as S1-nuclease mapping or primer repair analysis. *E. coli* transformants incorporating the isolated gene on a plasmid are assayed to confirm the presence of DHPS activity and the in vitro relative sensitivity of enzymic activity to added L-lysine.

As exemplified hereinbelow, in order to isolate maize DHPS cDNA clones and generate altered forms of this crucial enzyme, direct genetic selection of maize cDNAs in an *Escherichia coli* dap A⁻ auxotroph lacking detectable DHPS activity was used. A pUC13 maize cDNA library was employed to complement the *E. coli* deletion mutant as had been used to isolate maize glutamine synthetase cDNA clones by D. P. Snustad et al., *Genetics*, 120, 1111 (1988). Five apparently identical DHPS cDNA clones were obtained. The cDNA expression product in these transformants was verified as DHPS by (i) expression of maize DHPS activity, which has characteristics distinct from *E. coli* DHPS, (ii) identification of an open reading frame of the size expected for the monomeric subunit, and (iii) agreement of the cDNA sequence with the N-terminal amino acid sequence of the purified maize enzyme.

The DNA encoding the *Zea mays* DHPS can then be mutated by exposing the *E. coli* transformants to ultraviolet light, x-rays, gamma radiation or to chemical agents such as nitrosoamines, or alkylsulfonates, and selecting for AEC-resistant colonies. The DHPS activity expressed by AEC-resistant colonies is then tested for lysine inhibition to confirm that the mutations confer reduced feedback inhibition of *Zea mays* DHPS.

The cDNA sequences corresponding to the mature polypeptide region of the lysine-insensitive DHPS mutants are then determined and compared to the parental wildtype cDNA, to locate the nucleotide base changes which in turn result in alterations of the native *Zea mays* DHPS amino acid sequence, which impart resistance to feedback-inhibition by lysine. In three instances, single amino acid substitutions in the native sequence were found to impart a substantial degree of lysine resistance.

All lysine biosynthetic enzymes studied in plants to date have been localized in the chloroplasts. Thus, to accomplish proper localization of the altered DHPS, a second DNA fragment encoding a chloroplast transit peptide sequence is attached to the 5' terminus of the DNA sequence coding for the altered DHPS, in the proper reading frame, whereby a complete transit peptide-DHPS preprotein will be translated from transcripts of the gene fusion. Useful transit peptides (typically 40 to 70 amino acids in length) function post-translationally to direct the preprotein to the chloroplast, where the preprotein is imported in an energy-dependent process. The amino acid sequence of a *Zea mays* transit peptide is given in SEQ ID No. 5. The transit peptide is cleaved either during or just after import to yield the mature polypeptide. If the DNA sequence encoding the altered DHPS is derived by in vitro mutation of a wildtype *Zea mays* gene, the native *Zea mays* CTP-encoding DNA sequence (SEQ ID No. 4) may be isolated from the maize genome along with the DHPS gene and retained as a part of the total DNA during the cloning/mutation procedures.

If necessary, the DNA fragment encoding this transit peptide can be obtained from a variety of plant nuclear genes, so long as the products of said genes are expressed as preproteins comprising an amino-terminal transit peptide and transported into chloroplasts. Examples of plant gene products known to include such transit peptide sequences are the small subunit of ribulose bisphosphate carboxylase, ferredoxin, chlorophyll a/b binding protein, chloroplast ribosomal proteins encoded by nuclear genes, certain heat shock proteins, amino acid biosynthetic enzymes such as acetohydroxy acid synthase and 3-enolpyruvylphosphoshikimate synthase, and the like. Alternatively, the DNA fragment coding the transit peptide may be chemically synthesized either wholly or in part from the known sequences of transit peptides, such as those listed hereinabove.

Regardless of the source of the DNA fragment coding the transit peptide, it should include a translation initiation codon and encode an amino acid sequence that is recognized by and will function properly in chloroplasts of the host plant. Attention should also be given to the amino acid sequence at the junction between the transit peptide and the mature DHPS subunit where the preprotein is cleaved to yield mature DHPS. Certain conserved amino acid sequences have been identified and may serve as a guideline. Precise fusion of the transit peptide coding sequence with the DHPS coding sequence may require manipulation of one or both DNA sequences to introduce, for example, a convenient restriction site. This may be accomplished by methods including site-directed mutagenesis, insertion of a chemically synthesized oligonucleotide linker, and the like.

Likewise, expression of the altered maize DHPS in plant cells requires regulatory sequences that are recognized by and functional in plant cells, i.e., in cultured *Zea mays* cells. These sequences include a 5' transcriptional initiation region and 3' translational and transcriptional termination regions. The 5' transcriptional initiation region will include the RNA polymerase binding site (promoter). Plant promoters of different kinds are known which are derived from both mono- and dicotyledonous plants, and which are both non-tissue-specific and tissue-specific. The preferred promoter is the cauliflower mosaic virus (CaMV) 35S promoter, which is commercially available, and is generally expressed in most, if not all, plant tissues (H. Guilley et al., *Cell*, 39, 763 (1982); J. T. Odell et al., *Nature*, 313, 810 (1985)). Other promoters that can be used are inducible promoters, like the light-inducible promoter derived from the pea rbcS gene (G. Coruzzi et al., *EMBO J.*, 3, 1671 (1984)) and the actin promoter from rice (D. McElroy et al., *The Plant Cell*, 2, 163 (1990)). Tissue-specific promoters are used to direct lysine overproduction in tissues consumed for food, such as seeds in cereals and tubers in potatoes. Seed-specific promoters, such as phaseoline promoter from beans, shown to be expressed in a seed-specific manner in transgenic tobacco plants, (C. Sengupta-Gopalan, *Proc. Natl., Acad. Sci. USA*, 82, 3320 (1985)) may be used. For the expression in potato tubers, a promoter derived from the potato patatin gene may be used. It may also include regions required for regulation of transcription where the regulation is mediated by chemical or physical induction or repression.

Examples of such regulation include light-induced expression of ribulose bisphosphate carboxylase small subunit, heat-induced expression of heat shock proteins, genes regulated by plant hormones or other metabolites, developmentally regulated expression, wound- or stress-induced expression, and the like.

The 5' sequences may also include transciptional enhancer sequences, such as the maize Adh1 intron. The 5' regions may be native to the host plant, or may be derived from other plants where the sequences are functional in the host plant. Suitable sequences may also be obtained from genes of the Ti plasmid of *Agrobacterium tumefaciens*, including octopine synthase, nopaline synthase, mannopine synthase, and the like, or may be obtained from certain viral genes. Alternatively, the transcriptional initiation region may be chemically synthesized.

The 3' region will include transcriptional termination sequences and may include polyadenylation signal sequences. This region may be derived from the same gene as the 5' sequences or from a different gene. These sequences may also be chemically synthesized.

Thus, the present resultant expression cassette can comprise a 5' transcriptional initiation region, a chloroplast transit peptide coding sequence, the altered *Zea mays* DHPS coding sequence, a translational stop codon, and a 3' transcriptional termination region. The cassette will usually include less than five kilobases, and preferably will include between two and three kilobases.

The choice of a vector for introducing the present DHPS expression cassette into plant cells will depend on the choice of the transformation method which will, in turn, depend on the host plant and the choice of plant tissue source.

The expression vector comprising the chimeric gene or the "naked" chimeric gene is then introduced into plant cells. Any transformation protocol capable of transferring DNA to either monocotyledonous or dicotyledonous plant cells can be used. Examples are: transformation by direct DNA transfer into plant cells by electroporation (DeKalb Plant Genetics, published PCT application WO 92/12250; R. A. Dekeyser et al., *The Plant Cell*, 2, 591 (1990)); direct DNA transfer to plant cells by PEG precipitation (A. Hayashimoto et al., *Plant Physiol.*, 93, 857 (1990)); direct DNA transfer to plant cells by microprojectile bombardment (D. E. McCabe et al., *Bio/Technology*, 6, 973 (1988); W. J. Gordon-Kamm et al., *The Plant Cell*, 2, 603 (1990)); and DNA transfer to plant cells via infection with Agrobacterium. The preferred method for dicot transformation is via infection of plant cells with *Agrobacterium tumefaciens* using the leaf-disk protocol (R. B. Horsch et al., *Science*, 227, 1229 (1985)). Monocots such as *Zea mays*, can be transformed via microprojectile bombardment of embryogenic callus tissue or immature embryos, or by electroporation following partial enzymatic degradation of the cell wall with a pectinase-containing enzyme (PCT WO 92/12250).

Methods such as microprojectile bombardment or electroporation are carried out with "naked" DNA where the expression cassette may be simply carried on any *E. coli* cloning vector such as plasmids pBI221, pGEX-2T, pBARGUS, pBR322, pRK290, pACYC184, and the like. In the case of viral vectors, it is desirable that the system retain replication functions, but lack functions for disease induction.

Regardless of the choice of vector or transformation protocol, identification of transformed plant cells is facilitated by including a gene encoding a function that is selectable in plant cells. Preferred genes are those encoding resistance to a chemical normally inhibitory to plant cells, such as resistance to hygromycin, kanamycin, methotrexate, and certain herbicides such as glyphosate (aroA) or phosphinothricin (bar). The selectable marker may be carried on a separate plasmid that is co-transformed with the DHPS-bearing plasmid, or may be carried on the same plasmid as the DHPS cassette.

Alternatively, a screenable marker or "reporter gene" such as the β-glucuronidase (GUS) gene may be used in place of a selectable marker. Cells transformed with this gene may be identified by the production of a blue product on treatment with 5-bromo-4-chloro-3-indolyl-β-D-glucuronide (X-Gluc).

For example, the pBARGUS plasmid (M. E. Fromm et al., *Bio/Technology*, 8, 833 (1990)) contains the selectable marker gene for phosphinothricin (BASTA) resistance under control of the 35S promoter (plus corn Adh1 intron) as well as a separate gene for the visual marker GUS under control of the Adh1 promoter (plus Adh1 intron). This plasmid is particularly useful for co-transformation with a plasmid bearing the CTP-DHPS gene construct. The pBI221 plasmid vector (Clontech) can be used to place the corn DHPS coding sequence under the control of the CaMV 35S promoter. The complete DHPS sequence including the transit peptide sequence is preferably amplified by PCR using primers containing terminal restriction sites. The pBI221 plasmid is cut with Bam HI and Sst1 to remove the β-glucuronidase (GUS) marker gene sequence and the rest of the plasmid containing the 35S promoter and NOS 3' termination region can be recovered after gel separation. The corn DHPS sequence can then be cloned into the vector in place of the GUS marker. The structure of the final pBI221-35S:DHPS plasmid can be verified by sequencing starting in the 35S promoter through the DHPS sequence to ensure that PCR amplification had not generated unwanted mutations. Auxotrophic *E. coli* cells transformed with these constructs will grow very slowly on minimal medium, indicating DHPS expression.

Transformation vectors containing a zein promoter can also be constructed and used to test for tissue-specific expression in developing endosperm tissue. The 35S promoter regions of the pBI221-35S:DHPS-WT (wildtype) and pBI221-35S:DHPS-M1 (mutant) constructs can be replaced with a 1563-bp promoter sequence from a genomic clone (Z36B) for a 22-kD zein-associated protein. See R. E. Mitchell, Ph.D. Thesis, University of Minnesota (1992). The 1563-bp promoter in this construct contains a "7-11-7" motif (a 7 bp conserved sequence, CAACAAA; an 11 bp nonconserved spacer; a second 7 bp conserved sequence, ATGTCAA) found in all sequenced members of the 19-kD class of zein. This particular zein promoter has not been tested for expression in stable transformants of corn, but it has shown relatively good transient expression of chloramphenicol acetyltransferase (CAT) activity in endosperm cells of developing kernels bombarded with a ZEIN:CAT construct compared to bombardment with a 35S:CAT construct.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryogenic maize callus and immature embryos are preferred *Zea mays* tissue sources.

The transformation is carried out under conditions directed to the plant tissue of choice. The plant cells or tissue are exposed to the DNA carrying the DHPS expression cassette for an effective period of time. This may range from a less-than-one-second pulse of electricity for electroporation, to a two-to-three day co-cultivation in the presence of plasmid-bearing Agrobacterium cells. Buffers and media used will also vary with the plant tissue source and transformation protocol. Many transformation protocols employ a feeder layer of suspended culture cells (tobacco or Black Mexican Sweet, for example) on the surface of solid media plates, separated by a sterile filter paper disk from the plant cells or tissues being transformed.

Following treatment with the DNA, the plant cells or tissue may be cultivated for varying lengths of time prior to selection, or may be immediately exposed to a selective agent such as those described hereinabove. The media used in the selection may be formulated to maintain transformed callus or suspension culture cells in an undifferentiated state, or to allow production of shoots from callus, leaf or stem segments, tuber disks, and the like.

Cells or callus observed to be growing in the presence of normally inhibitory concentrations of the selective agent are presumed to be transformed and may be subcultured several additional times on the same medium to remove non-resistant sections. The cells or calli can then be assayed for the presence of the DHPS gene cassette, or may be subjected to known plant regeneration protocols. In protocols involving the direct production of shoots, those shoots appearing on the selective media are presumed to be transformed and may be excised and rooted, either on selective medium suitable for the production of roots, or by simply dipping the excised shoot in a root-inducing compound and directly planting it in vermiculite.

In order to produce transgenic plants exhibiting elevated free lysine levels, the gene must be taken up into the plant cell and stably integrated within the plant genome. Plant cells and tissues selected for their resistance to an inhibitory agent are presumed to have acquired the gene encoding this resistance during the transformation treatment. Since this marker gene is commonly linked to the DHPS gene, it can be assumed that the DHPS gene has similarly been acquired. Southern blot hybridization analysis using a probe specific to the DHPS synthase gene can then be used to confirm that the foreign gene has been taken up and integrated into the genome of the plant cell. This technique may also give some indication of the number of copies of the gene that have been incorporated. Successful transcription of the foreign gene into mRNA can likewise be assayed using Northern blot hybridization analysis of total cellular RNA and/or cellular RNA that has been enriched in a polyadenylated region. For example, embryogenic cell lines derived from immature *Zea mays* embryos can be transformed by accelerated particle treatment essentially as described by Gordon-Kamm et al. (1990) cited above. Excised immature embryos can also be used as the target for transformation prior to tissue culture induction, selection and regeneration as recently reported by M. S. Koziel et al., *Bio/Technology*, 11, 194 (1993) for an inbred line. They reported an average transformation frequency of approximately 1% (one transformed plant per 100 embryos) or one plant per 2.5 bombardments.

Plasmid DNA of the pBARGUS selection vector can be mixed with an equal amount of DNA of the construct containing the altered DHPS gene such as pBI221-35S:DHPS-M1 and coated onto tungsten particles. Following bombardment, the cultures are maintained on standard culture medium for 3 days and then transferred to selection medium containing 3 mg/L phosphinothricin. Surviving cultures can be maintained on selection medium by transferring every two weeks. When sufficient tissue is obtained for each putative phosphinothricin-resistant cell line, a portion (ca. 100–200 mg) is used for DNA extraction. Southern blots can be hybridized with a probe specific to the bar or other marker gene and a probe that identifies fragments of the correct size for the nonselected DHPS transgene. These tests will verify cell lines transformed with the selectable phosphinothricin resistance bar gene and identify cell lines that are also co-transformed with the CTP-DHPS transgene of interest.

Once transcribed, the mRNA must be translated by the plant ribosomes into DHPS synthase subunit, which must in turn be able to assume a three-dimensional configuration that will confer catalytic activity. Plant cells or tissues shown both to carry and transcribe the altered DHPS synthase gene may be further characterized by extraction of the cells or tissues and demonstration of lysine-tolerant DHPS synthase activity. This in vitro lysine tolerance is readily distinguishable from the more highly lysine-sensitive native DHPS synthase activity which can be extracted from control plant cells or tissues. Depending on the transcriptional initiation and regulatory sequences used in the construction of the cassette, the activity may be detected in all plant tissues, in selected tissues, or only under selected inducing conditions.

The ability of the altered DHPS synthase to participate in lysine biosynthesis may be assessed by determining the relative tolerance of plant cells or tissues to the lysine analog S-(2-aminoethyl)cysteine (AEC). Like lysine, AEC is a potent inhibitor of plant DHPS synthase. Plants cells or tissues exposed to inhibitory concentrations of AEC are effectively starved for lysine. The present altered DHPS, however, is considerably less sensitive to this inhibition. The ability of plant cells or tissues expressing active DHPS to tolerate normally inhibitory concentrations of AEC strongly suggests that the enzyme is functioning properly in the biosynthesis of lysine.

If the altered DHPS is contributing to the biosynthesis of lysine, and if no other mechanisms act to regulate the free lysine pool, free lysine may accumulate to levels higher than seen in control plant cells or tissues. Free amino acid levels may be readily measured by techniques such as reverse phase HPLC analysis of trichloroacetic acid (TCA) extracts of transgenic plant cells or tissues.

Plants that accumulate significantly elevated levels of free lysine in accord with these mechanisms are grown to maturity. These plants are allowed to flower and are self-pollinated or crossed to an appropriate parental line to obtain seed. This seed may then be analyzed for inheritance of the desired trait.

An initial screen of the seed may be germination and seedling growth in the presence of concentrations of AEC that will inhibit the growth of seedlings germinated from control seed. Seedlings demonstrating AEC tolerance may be grown to maturity and fully characterized as described hereinabove for the original regenerate plants.

Preferably, male-fertile regenerated plants will be self-pollinated and crossed to control female plants; any male-sterile plants will be pollinated by control plants. A small sample (6–8) of developing or mature kernels can be stained for GUS activity to confirm genetic transmission and segregation of the marker gene. Seeds from these crosses will be planted and the transgenic seedlings identified by GUS assays and confirmed by Southern blot analysis. Progeny plants confirmed to contain the transgene(s) of interest will be grown to maturity and used in further crosses and tests to develop defined transgenic genotypes.

Self-pollination of a hemizygous transgenic regenerated plant should produce progeny equivalent to an F2 in which approximately 25% should be homozygous transgenic plants. Self-pollination and testcrossing of the F2 progeny to nontransformed control plants will be used to identify homozygous transgenic plants and to maintain the line. If the progeny initially obtained for a regenerated plant were from crosspollination, then identification of homozygous transgenic plants will require an additional generation of self-pollination.

Preliminary biochemical analyses can be carried out on this early generation. An accurate assessment of the free pool and total concentrations of lysine and other amino acids can be obtained for a bulked sample of 10 kernels on a self-pollinated ear of a transgenic regenerated plant. Since one of the most important considerations is to compare lysine concentrations in kernels of control genotypes with those of genotypes containing lysine-insensitive DHPS transgenes, these analyses will be done as early as possible. Subsequent development of homozygous transgenic lines permit determination of: (i) the total enzyme quantity and activity in various plant tissues, (ii) the extent of lysine inhibition of enzyme activity, and (iii) the relationships with lysine concentration.

Plants that may be improved by such a transformation include but are not limited to processed plants (soybeans, canola, potatoes, tomatoes, lupins, sunflower and cottonseed), forage plants (alfalfa, clover and fescue), and the grains (maize, wheat, barley, oats, rice, sorghum, millet and rye). The plants or plant parts may be used directly as feed or food or the lysine may be extracted for use as a feed or food additive.

The invention will be further described by reference to the following detailed examples wherein the DHPS-deficient *E. coli* dapA$^-$ mutant AT997 characterized by P. Yeh et al., *Mol. Gen. Genet.*, 212, 105 (1988) was obtained from the *E. coli* Genetics Stock Center, Yale University. Strain AT997 required diaminopimelic acid (DAP) for growth and was routinely maintained on LB medium (See *Molecular Cloning*) supplemented with 100 μM DAP. Nonmutant laboratory strains were MV1190 and 71–18. Vectors for sequencing and RNA synthesis were pUC119 (J. Vieira et al., *Methods Enzyml.*, 153, 3 (1987), pTZ18U (D. A. Mead et al., *Protein Engineering*, 1, 67 (1986) and pJKKmf[–] (see J. A. Kirschman et al., *Gene*, 68, 163 (1988).

EXAMPLE 1

Isolation of DHPS cDNA Clones

A cDNA library constructed as described by D. P. Snustad et al., *Genetics*, 120, 1111 (1988) from polyA$^+$ RNA of Black Mexican Sweet maize suspension cell cultures was obtained from J. P. Hunsperger and I. Rubenstein (Dept. Plant Biology, University of Minnesota). The cDNAs had been fractionated into 10 size classes and were ligated into the EcoRI site of pUC13. Plasmid DNAs from fractions, 4, 5 and 6 (average insert sizes of 1.9, 1.4 and 1.0 kb, respectively) were used to transform AT997dapA$^-$ cells with an electroporator (800 V, 5 ms, 0.56 mm electrode gap; BTX Industries, San Diego, Calif.). Cells were prepared for electroporation by the procedure of W. J. Dower et al., *Nucl. Acids Res.*, 16, 6127 (1988) and, following transformation, were grown for 1 hr at 37° C. in SOC medium (see *Molecular Cloning*) containing 100 μM DAP. Cells were then washed twice in M9 medium (see *Molecular Cloning*) and plated on LB, LB+50 μg/ml ampicillin, LB+100 μM DAP, and LB+100 μM DAP+50 μg/ml ampicillin.

Cell viability was confirmed by growth on LB+DAP and transformation frequency was confirmed by growth on LB+DAP+ampicillin. Cells growing on M9+ampicillin or LB+ampicillin medium were assumed to be complemented because of the strict requirement of AT997dapA$^-$ for DAP. Growing colonies were restreaked onto fresh LB+ampicillin medium to obtain single cell colonies. Single colonies were inoculated into LB medium and grown for plasmid isolation (see *Molecular Cloning*). The original AT997dapA$^+$ strain was retransformed with the purified plasmid DNA to confirm the complementation.

The transformation frequency of AT997dapA$^-$ cells by electroporation ranged from 10$^6$ to 10$^8$ transformants per microgram of DNA. Revertants of the dapA$^-$ mutation were not detected on minimal medium at any time during this study. When the *E. coli* AT997dapA$^-$ auxotroph was transformed with fractions 4, 5 and 6 of the pUC13 maize cDNA library and plated onto minimal medium, five colonies grew without exogenous DAP. All five functional colonies contained plasmids from fraction 5 (1.4 kb average insert size), which appeared to be identical based on digestion with the restriction endonucleases EcoRI, SmaI and PvuII (data not shown). When AT997dapA$^-$ cells were retransformed with purified recombinant plasmid DNA from each of these clones, the complementation frequency was approximately the same as the transformation frequency. These results confirmed that the plasmids containing maize cDNA were responsible for growth of transformed AT997 cells on minimal medium and that colonies observed were not due to reversion of the dapA$^-$ gene.

EXAMPLE 2

Enzyme Assays

Crude lysates from wildtype 71-18dapA$^+$ cells, AT997dapA$^-$ transformed with pUC13 lacking a cDNA insert, and the five complementing transformant cell lines AT997(pZM DHPS1) to AT997(pZM DHPS5) were assayed for DHPS activity. The transformed cells were grown overnight in M9 medium+100 μM DAP, collected by centrifugation at 5000×g for 10 min and resuspended in 1/10 volume of extraction buffer (100 mM TRIS-HCl, pH 8.0, 100 mM NaCl, 100 mM pyruvate). Cells were placed briefly on ice, disrupted by sonication (60 W, 15 s) and debris removed by centrifugation at 15000×g for 15 min. The supernatant was desalted on a G25 Sephadex column equilibrated with 10 mM TRIS-HCl, pH 8.0 and 1 mM EDTA and used for enzyme assays.

The DHPS assay buffer (R. M. Wallsgrove et al., *Phytochem.*, 20, 2651 (1981)) contained 100 mM TRIS-HCl, pH 8.0, 10 mM pyruvate, 1.4 mM aspartate semialdehyde neutralized just prior to use, and 100 μl enzyme in a final volume of 250 μl. Tubes were incubated at 37° C. for 30 min and reactions stopped by addition of 1 ml of 0.22M sodium citrate, 0.55M sodium phosphate, pH 5.0 and 0.25 mg/ml-aminobenzaldehyde. The colored reaction product was allowed to form for 3 hr at 37° C. and samples were centrifuged at 10000 g. Activity units (0.001 OD/min) were determined at 520 nm; standard errors of replicate assays were routinely <2% of the mean. The data is summarized on Table 1, below.

TABLE 1

| E. Coli Cell Line | Protein (mg/ml) | Specific Activity[a] Control | Specific Activity[a] 100 μM Lysine | % Inhibition |
|---|---|---|---|---|
| 71-18dapA+ | 126 | 130 | 120 | 8 |
| AT997dapA− | 82 | nd[c] | nd | — |
| AT997dapA−(pUC13) | 104 | nd | nd | — |
| AT997dapA−(pZM DHPS1) | 103 | 230 | 24 | 90 |
| AT997dapA−(pZM DHPS2) | 109 | 160 | 15 | 91 |
| AT997dapA−(pZM DHPS3) | 105 | 190 | 22 | 88 |
| AT997dapA−(pZM DHPS4) | 103 | 300 | 42 | 86 |
| AT997dapA−(pZM DHPS5) | 102 | 260 | 27 | 90 |
| Purified maize DHPS[b] | — | 250 | 8 | 97 |

[a]Specific activity, 0.001 OD$_{520}$/min per milligram protein × 1000.
[b]Protein concentrations and specific activity values were not determined for the highly purified maize DHPS preparation; therefore, the data are from control and inhibited assays containing units of DHPS activity similar to the units in *E. coli* extract assays.
[c]nd, activity not detected.

As shown by the data in Table 1, no DHPS activity was detectable in crude lysates obtained from AT997dapA− or AT997dapA− cells transformed with pUC13, indicating that the cDNA insert was responsible for complementation of the dapA− lesion, and not the vector alone. The specific activities of DHPS from wildtype 71-18dapA+ cells and the five transformant lines were similar when lysine was not included in the assay. DHPS from the five transformants, however, was inhibited 86% to 90% in the presence of 100 μM lysine, whereas wildtype *E. coli* DHPS from 71-18dapA+ was only inhibited 8%. Purified DHPS from Black Mexican Sweet maize was inhibited 97% by 100 μM lysine.

This difference in lysine sensitivity was an additional indication that the cDNA inserts were from maize and that restoration of DHPS activity in the *E. coli* mutant was not caused by reversion of the dapA− allele or due to an interaction with pUC13 plasmid DNA. In preliminary tests of partially purified DHPS from cell line pZM DHPS5, the $[I]_{0.5}$ value for lysine was determined to be in the range of 20 to 30 μM. This value corresponds to the $[I]_{0.5}$ value of 23 μM lysine for highly purified DHPS from maize cells determined by D. A. Frisch et al., *Plant Physiol.*, 96, 444 (1991), and indicates that the lysine inhibition properties are quite similar.

EXAMPLE 3

Subcloning, Template Preparation and DNA Sequence of Maize DHPS Gene

The pZM DHPS cDNAs were subcloned into the EcoRI site of pUC119 in both orientations and a set of overlapping subclones was generated for each orientation by unidirectional deletion by the methodology of J. Vieira et al., *Methods Enzymol.*, 153, 3 (1987). Sequencing reactions were performed with Sequenase (U.S. Biochemical Corp.) using [α-$^{35}$S]dATP as the labeled nucleotide according to the protocol provided by the manufacturer.

Figure 2:
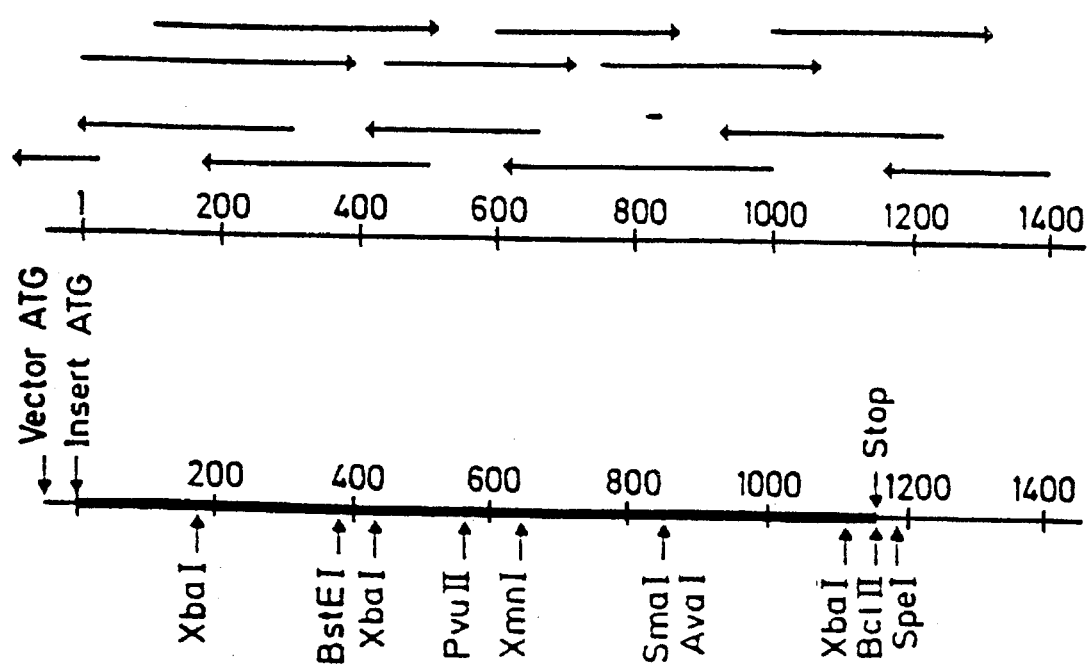
FIG. 2 is a schematic depiction of the deletion subclones of pZM DHPS5 used for nucleotide sequencing and the restriction map of maize DHPS based on sequence analysis.

The deletion subclones for pZM DHPS5B are shown in FIG. 2 and the complete cDNA sequence based on both strands is shown in FIG. 3; SEQ ID No. 6.

The putative start of the coding region for maize DHPS was established by comparison of the N-terminus amino acid sequence of SDS-PAGE purified DHPS monomer with the amino acid sequence derived from the nucleotide sequence. DHPS was purified more than 4000-fold with 25% recovery from Black Mexican Sweet maize suspension cultures by the procedure of D. A. Frisch et al., *Plant Physiol.*, 96, 444 (1991). Only one protein band (ca. 130000 $M_r$) was detected by silver-staining after native polyacrylamide gel electrophoresis (PAGE) and this band corresponded to the position of DHPS activity. The 38000 $M_r$ monomeric polypeptide was purified by SDS-PAGE (W. K. Laemmli, *Nature*, 227, 680 (1970)) and blotted onto Immobilon P (Millipore) membrane with 50 mM 3-[cyclohexylamino]-1-propanesulfonic acid; pH 10.0, 0.1% (w/v) SDS and 10% (v/v) methanol. The polypeptide band corresponding to the DHPS monomer was cut out of the membrane. N-terminal sequencing was performed by the Microchemical Facility, University of Minnesota, using an Applied Biosystems 470 gas phase peptide sequenator, by the procedure of P. Matsudiana, *J. Biol. Chem.*, 262, 10035 (1987).

The apoprotein for DHPS should contain an N-terminus transit sequence to facilitate transport into the chloroplast, but this sequence was not expected to be present in the purified mature DHPS. The N-terminus sequence, Ala-Ile-Thr-Leu-Asp-Asp-Tyr-Leu, of the purified protein was identified in the cDNA sequence between +163 and +186 as illustrated in FIG. 3. The nearest in-frame 5' ATG was located 162 bp upstream indicating that the transit peptide consisted of at least 54 amino acids. The putative 54 amino acid transit sequence for maize DHPS (FIG. 3; SEQ ID No. 5) contains nine serines and four threonines (24%), seven alanines, four valines and no acidic amino acids in agreement with the general features of plastid transit polypeptides. In addition, comparisons of maize and wheat DHPS transit sequences show no homology except in the region immediately adjacent to the start of the mature protein where there are 3/6 and 6/8 matches, respectively, for wheat cDNA clones, pDA17 and pDA26. In contrast, when the amino acid sequence for the mature maize DHPS (position 163 to 1140; SEQ ID No. 8) is compared with the two wheat cDNAs, the lengths of the mature polypeptides are the same (326 amino acids) and there is 86% to 88% homology at the amino acid level.

Only one orientation of the DHPS cDNA complemented AT997dapA$^-$ indicating that transcription originated from the pUC13 lacZ promoter. The β-galactosidase translation initiation codon and the ATG at position +1 (FIG. 3) of DHPS were in the same reading frame. Hence, it is likely that DHPS activity is expressed by a fusion protein that contains, in addition to the 380 amino acids of the maize cDNA coding region, 5 N-terminal amino acids derived from β-galactosidase, 18 amino acids from the vector polylinker sequence and 13 amino acids from the normally nontranslated 5∝ region of the maize DHPS cDNA. When the cDNA was ligated into a different expression vector (pGEX-2T, Pharmacia), the fusion protein, which contained more than 200 amino acids from glutathione S-transferase, also had DHPS activity. These results indicate that additional amino acids at the N-terminal region do not alter the enzyme conformation sufficiently to eliminate DHPS catalytic activity.

If pZM DHPS5 is not a full-length cDNA, then the authentic translation start site for the DHPS apoprotein should be at another ATG at least 39 bp further upstream but in the same reading frame. Based on the sequence of pZM DHPS5B, the complete coding sequence for the DHPS apoprotein is 1140 bp long. The predicted $M_r$ for the mature protein is 35854 which is similar to the 38000 $M_r$ estimate obtained from SDS-PAGE. The 2200 $M_r$ difference could indicate posttranslational modification of the mature DHPS subunit. The ATG for the β-galactosidase gene in the pUC13 expression vector was also in the same reading frame 108 bp upstream (FIG. 3) of the +1 ATG. Translation of cDNA transcripts in transformed AT997dapA$^-$ cells either initiated at the authentic maize ATG or the additional 36 amino acids in the fusion protein did not interfere with DHPS activity or prevent feedback inhibition by lysine.

EXAMPLE 4

Northern and Genomic Blot Hybridizations of Maize DHPS

Endosperms and embryos were dissected from immature maize kernels 12 days after pollination, frozen separately in liquid nitrogen and total RNA extracted by the procedure of J. Logsmann etal., *Anal. Biochem.*, 163, 16 (1987). Following electrophoresis through 1.4% agarose gels containing 6% (v/v) formaldehyde (G. F. Gerard et al., *Focus*, 8, 5 (1986)), RNA was transferred overnight to Zeta Probe (Bio-Rad) nylon filters according to the manufacturer's recommendations.

Genomic DNA was isolated from leaf tissue of 14-day-old seedlings of maize inbred line A619 by the procedure of M. A. Saghai-Maroof et al., *PNAS USA*, 81, 8041 (1984). DNA was digested with restriction enzymes, electrophoresed through 0.8% agarose gels and transferred to Gene Screen (DuPont) nylon filters for Southern blotting. RNA and DNA gel blots were prehybridized for at least 2 hr and hybridized overnight at 65° C. using standard conditions.

RNA probes were prepared by strand-specific transcription of DHPS cDNA subcloned into pJKKmf[−] (See J. A. Kirschman etal., *Gene*, 68, 163 (1988). DNA probes were made by random-primer labeling 100 ng of agarose gel-purified DHPS cDNA by the procedure of A. P. Feinberg etal., *Anal. Biochem.*, 132, 6 (1983). Final post-hybridization washes were in 30 mM NaCl, 3 mM sodium citrate and 0.1% (v/v) SDS at 65° C.

Hybridization of pZM DHPS5 cDNA to RNA gel blots indicated that DHPS transcripts of approximately 1.4 kb were present in 12-day-old developing maize embryos and endosperm. Transcripts of this size would be large enough to include the coding region plus the nontranslated 5' sequence and a 3' poly(A) tail. The relative abundance of DHPS transcripts was similar for samples at 10, 14 and 16 days after pollination (data not shown), but also appeared to be consistently higher in embryos than in endosperm tissue.

Hybridization of pZM DHPS5 cDNA to DNA gel blots of maize genomic DNA digested with HindIII, BamHI or EcoRI revealed a single prominent band in each digest ranging from >10 kb to about 5 kb. The pZM DHPS5 cDNA sequence did not contain restriction sites for these enzymes indicating that the single prominent bands probably contained the entire DHPS coding region. The lack of a second prominent band also indicated that any potential introns were not likely to contain these restriction sites. Each digest also had two or three less intensely hybridizing bands of about 4 kb to over 20 kb indicating the presence of additional genomic sequences with at least partial homology to the cloned maize DHPS.

EXAMPLE 5

Selection for Altered Forms of Maize DHPS Based on AEC Resistance

To obtain altered forms of maize DHPS, AT997 cells were mutagenized with ethyl methanesulfonate (EMS) and then subjected to selection for growth in the presence of the lysine analog S-2-aminoethyl L-cysteine (AEC). AEC inhibits the enzyme activity of maize DHPS and, consequently, the growth of transformed AT997 cells. AT997dapA$^-$ cells transformed with plasmid DHPS5B were grown on 1×A minimal medium (J. H. Miller, *Experiments in Molecular Genetics*, Cold Spring Harbor Laboratory (1972) at pages 431–433, hereinafter "Miller, 1972") to a density of 2 to 3×10$^8$ cells/ml. These cells were resuspended in 1×A medium lacking glucose, treated with 18 mM ethyl methane sulfonate for 2 hr, washed with 1×A medium and grown at 37° C. for 8 to 10 hr in M9 medium (see *Cloning Manual*). Cells were then plated on M9 medium containing 10 mM AEC and 50 μg ml$^{-1}$ ampicillin. After incubating the plates for 72 to 96 hr at 37° C., transformed colonies were picked, restreaked and grown for 72 to 96 hr on fresh M9 medium containing 10 mM AEC and 50 μg ml$^{-1}$ ampicillin.

To ensure that the growth of AT997 colonies on AEC medium was due to alterations in the maize pZM DHPS5B plasmid, plasmid DNA from single-cell-derived cultures was used to repeat the transformation of previously untransformed AT997dapA$^-$ auxotroph cells (Example 1). These new AT997 transformants were grown on the AEC selection medium and two cell lines (designated pZM DHPS-M1 and pZM DHPS-M2) were chosen for analysis of DHPS activity and lysine inhibition.

EXAMPLE 6

DHPS Extraction from Transformed AT997 Cells and Determination of Altered DHPS Activity AT997 cells (approximately 1 ml packed vol), containing plasmids pZM DHPS5B, pZM DHPS-M1 or pZM DHPS-M2, were extracted by sonication (60 W, 20 s) into 5 ml of density gradient and sequenced using [$\alpha$-$^{35}$S]dATP and Sequenase 2.0 (U.S. Biochemical Corp, Cleveland, Ohio) according to the supplier's instructions. Vector and internal DHPS-specific oligonucleotide primers were used to obtain the complete sequences for both strands. The sequences of the internal primers are given on Table 2, below, wherein the primer position is given according to nucleotide +1, FIG. 3.

TABLE 2

| 5' Primers: | | |
|---|---|---|
| #109–126 | CGACTCCCTTCAGGCCTC | (SEQ ID NO: 9) |
| #307–324 | GATTCTCTCATAAACATG | (SEQ ID NO: 10) |
| #478–504 | ACCAGAGAAGCCGTCCACGCAACAGAA | (SEQ ID NO: 11) |
| #694–711 | AACATGGCGGGTGTCAAGGAA | (SEQ ID NO: 12) |
| #904–912 | AAGCTGTCGCCCCTGATG | (SEQ ID NO: 13) |
| 3' Primers: | | |
| #259–279 | TGGCAAATAGGGGGTTTTAAC | (SEQ ID NO: 14) |
| #451–471 | GCTTCCTGTGTTGCCTATCAC | (SEQ ID NO: 15) |
| #664–684 | AGAAATCGCTAGAATAACTTC | (SEQ ID NO: 16) |
| #865–885 | CTCGCCTTTGTACATGAGGCT | (SEQ ID NO: 17) |
| #1087–1107 | TAGAACCTGGGCCTCCTTCTG | (SEQ ID NO: 18) | ice cold buffer containing (100 mM TRIS-HCl, pH 8.0, 100 mM NaCl, 50 mM pyruvate) and then centrifuged at 12×g for 10 min. The supernatant was placed in a water bath (60° C.) for 5 min, cooled to 4° C. and centrifuged. The resulting supernatant was desalted on a Sephadex G50 column in 10 mM TRIS-HCl, pH 8.0, and 1 mM EDTA.

DHPS activity was determined as described in Example 2 except that the reaction was stopped after 2 min; at longer reaction times, activity was not linear with time. The volume of enzyme was adjusted so that the absorbance at 520 nm increased approximately 0.1 A (=100 activity units) after 2 min for standard control assays. Lysine concentrations were varied from 0.01 mM to 1.0 mM in the presence of constant concentrations of the substrates pyruvate (20 mM) and aspartate semialdehyde (1.4 mM). The average of two or three assays were used to determine enzyme activity values and percent inhibition by lysine.

Figure 4:
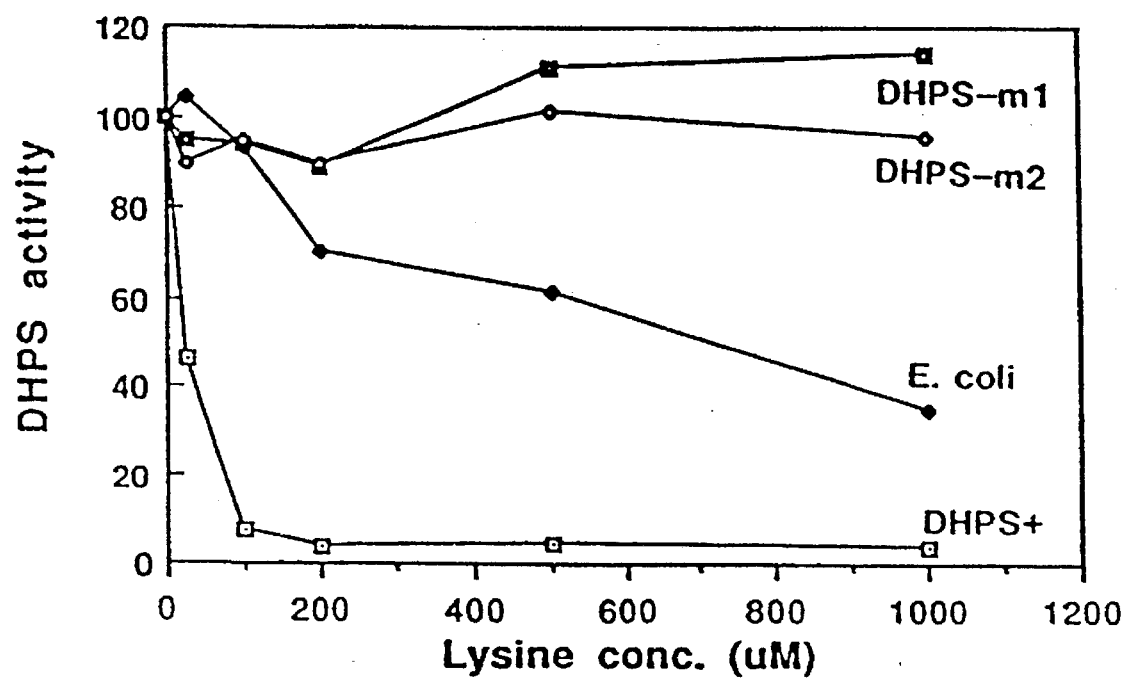
FIG. 4 is a graph depicting lysine inhibition of DHPS activity determined for wildtype (DHPS+) and mutant (DHPS-M1 and DHPS-M2) fusion proteins expressed in transformed AT997 *E. coli* compared to the DHPS activity of wildtype nontransformed *E. coli*.

As shown in FIG. 4, partially purified DHPS activity obtained from the selected AEC-resistant lines pZM DHPS-M1 and pZM DHPS-M2 was not inhibited by L-lysine concentrations as high as 1.0 mM. In contrast, DHPS activity from control AT997 cells containing the wildtype maize DHPS cDNA pZM DHPS5B was significantly inhibited by lysine concentrations as low as 25 µM which is similar to the concentration required to inhibit 50% of the activity of DHPS purified from maize cells. DHPS from wildtype, nontransformed E. coli strain DH5A showed an intermediate level of inhibition at lysine concentrations up to 1 mM. These analyses demonstrate that the AEC-resistant, transformed AT997 cells expressed a DHPS fusion protein that had DHPS activity clearly distinguishable from wildtype maize and E. coli DHPS and that it was highly insensitive to lysine inhibition.

EXAMPLE 7

Sequence Analysis of cDNAs Encoding Lysine-Insensitive Maize DHPS

The plasmid DNAs from two cell lines transformed with pZM DHPS-M1 DNA were purified on a cesium chloride The DNA sequences for both DNA preparations of pZM DHPS-M1 were identical and the sequence is shown in FIG. 5. Both strands of the cDNAs from mutant pZM DHPS-M1 were sequenced completely to identify positions at which the sequence differed from wildtype DHPS5B. Nucleotide #497 relative to the initiation ATG was the only position that differed from wildtype. Both mutant clones had GTA instead of GCA which would change the amino acid from an alanine to a valine residue. This amino acid change would be at position #112 relative to the amino-terminus of the mature DHPS polypeptide subunit, assuming the first 54 amino acids represent a transit peptide sequence cleaved upon translocation of the apoprotein into plastids. The fact that plasmid DNAs from two cell lines transformed with pZM DHPS-M1 both had the same mutation indicated that the plasmid preparation used for transformation of AT997 was homogeneous and not a mixture of different mutant plasmids. These data also demonstrated that single base-pair mutations can have a significant effect on the lysine inhibition properties of a maize fusion protein expressed in E. coli.

A sample of E. coli transformed with pZMDHPS-M1 has been deposited in the American Type Culture Collection, Rockville, Md. U.S.A. under the provisions of the Budapest Treaty under Accession No. ATCC 69294.

Additional independently derived mutations in maize DHPS were obtained by repeating the mutagenesis and selection protocol in separate experiments. Two different mutations in the maize DHPS structural gene have been identified that confer lysine insensitivity to the DHPS activity. Mutant plasmid pZM DHPS-M3 has a nucleotide change at position #496 (ACA instead of GCA); this change causes substitution of threonine for alanine at the same amino acid position (112) as altered in mutant pZM DHPS-M1. Mutant plasmid pZM DHPS-M4 has a nucleotide change at position #484 (AAA instead of GAA); this change causes substitution of lysine for glutamic acid at amino acid position #108.

EXAMPLE 8

Enzyme Properties of the Fusion Protein Derived from pZM DHPS5B and pZM DHPS-M1

The progenitor pZM DHPS5B cDNA clone and the derived pZM DHPS-M1 mutant cDNA clone both express a chimeric protein containing 90 additional amino acids at the amino-terminus. The fusion protein synthesized by transformed AT997 E. coli cells has extra amino acids not normally found in the mature maize DHPS polypeptide subunit. These extra amino acids do not interfere with DHPS catalytic activity or affinity for binding lysine, as shown in FIG. 4. DHPS assays of the partially purified, chimeric enzyme preparations were conducted with varying substrate concentrations (pyruvate from 0.5 to 50 mM; asparrate semialdehyde from 0.2 to 2.4 mM) and the activity values plotted on Lineweaver-Burke plots. Kinetic parameters derived from the data plots indicated that the substrate affinities were similar for wildtype and lysine-insensitive DHPS preparations. The kinetic properties of both fusion proteins were consistent with those determined for DHPS purified from maize.

EXAMPLE 9

Construction of Other Plasmids For Expression of Maize DHPS in E. Coli

To obtain cDNA clones of maize DHPS that did not contain the 36 extra amino acids at the amino-terminus, DHPS-specific primers containing BamHI or EcoRI linker sequences at the ends were used for PCR amplification of plasmid DNA from pZM DHPS5B or pZM DHPS-M1. The sequence of these primers is shown on Table 3, below.

TABLE 3

| PCR Primers | |
|---|---|
| 5'-End: CGCGGGATCCATGATTTCGCCGACGAATCTCC | (SEQ ID NO: 19) |
| 3'-End: CGATGAATTCCTAGTACCTACTGATCAACA | (SEQ ID NO: 20) |

The amplified products containing just the maize coding sequence for the apoprotein (mature polypeptide plus transit peptide) were cloned into the protein expression plasmid pGEX-2T (Pharmacia LKB, Pisacataway, N.J. U.S.A.) to form plasmids designated pGST:DHPS5Bapo and pGST:DHPS-M1-apo. The same procedure also was used to amplify just the maize sequence for the mature DHPS polypeptide and to clone it into pGEX-2T. These plasmids were designated pGST:DHPS5Bmat and pGST:DHPS-M1mat.

EXAMPLE 10

DHPS Polyclonal Antibody

The glutathione S-transferase:DHPS fusion protein was purified from AT997 cells transformed with pGST:DHPS5-Bapo by the procedure of Example 1. The fusion protein was purified on a glutathione-Sepharose affinity column (Pharmacia LKB) according to the supplier's instructions, cleaved with thrombin (0.5% [w/v], 1 hr, 25° C.) and the 42-kD DHPS apoprotein band was gel-purified from 12.5% acrylamide SDS gels. Monospecific polyclonal antisera against the purified DHPS apoprotein were obtained in rabbits according to standard procedures. Such antisera can be used to isolate both native and altered forms of Zea mays DHPS by affinity chromatography.

EXAMPLE 11

Construction of Plant Transformation Vectors Containing Wildtype and Altered Forms of Maize DHPS The coding sequences for maize DHPS apoprotein from pZM DHPS5B and pZM DHPS-M1 were transferred into several plasmids suitable for plant transformation. The complete DHPS sequence including the transit peptide sequence was amplified by the PCR using primers containing terminal restriction sites shown in Table 4.

TABLE 4

| 5'-End: CGCGGGATCCATGATTTCGCCGACGAATCTCC | (SEQ ID NO: 21) |
|---|---|
| 3'-End: CGCGGAGCTCCTAGTACCTACTGATCAACACG | (SEQ ID NO: 22) |

The pBI221 plasmid (Clontech, Palo Alto, Calif.) was digested with BamHI and SstI to remove the β-glucuronidase (GUS) marker gene sequence. The rest of the plasmid containing the 35S promoter and NOS 3' termination region was recovered after gel separation. The maize cDNA sequences for both wildtype and lysine-insensitive DHPS were force cloned into the vector in place of the GUS marker to produce plasmids designated pBI221-35S:DHPS5B and pBI221-35S:DHPS-M1. These plasmid sequences were verified by DNA sequencing starting in the 35S promoter through the DHPS sequence to ensure that PCR amplification had not generated unwanted mutations. AT997 auxotrophic cells transformed with these constructs grow very slowly on M9 minimal medium, indicating a low level of DHPS expression even though the plasmids lack a prokaryotic promoter.

Transformation vectors pBI221-ZEIN:DHPS5B and pBI221-ZEIN:DHPS-M1 were constructed by subcloning a maize zein promoter region into pBI221-35S:DHPS5B and pBI221-35S:DHPS-M1, respectively, in place of the 35S promoter. The 1,563-bp zein promoter region was obtained from a zein genomic clone, Z36B, described by R. E. Mitchell, in "Expression of Zein Associated Proteins," Ph.D. Thesis, U of Minnesota (1992). This promoter contains sequence motifs conserved in genes for a specific set of zein storage proteins expressed in maize endosperm tissue. These transformation constructs may result in endosperm-specific expression of the DHPS coding sequence in transformed maize plants.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of increasing the level of free L-lysine in a plant comprising:

(a) introducing a recombinant DNA sequence into the cells of a plant tissue source; wherein said recombinant DNA sequence comprises a first DNA sequence encoding an altered mature *Zea mays* dihydrodipicolinic acid synthase which is substantially resistant to feedback inhibition by endogenously produced free L-lysine, wherein the alteration is at least one amino acid change in amino acid residues 100 to 125 of a mature dihydrodipicolinic acid synthase operably linked to a second DNA sequence attached to the 5'-terminus of the first DNA sequence wherein said second DNA sequence encodes a chloroplast transit sequence that localizes the altered mature dihydrodipicolinic acid synthase in the chloroplasts of said cells and to a promoter functional in a plant cell; and (b) regenerating plants from said cells, wherein said recombinant DNA sequence is expressed in the cells of the plant.

2. The method of claim 1 wherein said second DNA sequence is a *Zea mays* chloroplast transit peptide DNA sequence.

3. A method of claim 1, wherein the first DNA sequence corresponds to SEQ ID No. 1.

4. The method of claim 1 wherein the amino acid sequence of the altered mature dihydrodipicolinic acid synthase corresponds to SEQ ID No. 2.

5. The method according to claim 1, wherein the cells of a plant tissue source are *Zea mays* cells.

6. A *Zea mays* cell comprising a recombinant DNA sequence including a first DNA sequence which expresses an altered mature *Zea mays* dihydrodipicolinic acid synthase which is substantially resistant to feedback inhibition by endogenously produced free L-lysine, wherein the alteration in the mature dihydrodipiclonic acid synthase is at least one amino acid change in amino acid residues 100 to 125 of a mature dihydropidicolinic acid synthase and which is operably linked to a second DNA sequence encoding a chloroplast transit peptide and to a promoter functional in a plant cell.

7. The *Zea mays* cells of claim 6 wherein the operably joined first and second DNA sequences correspond to SEQ ID No. 3.

8. The *Zea mays* cell of claim 6 wherein the amino acid sequence of the altered mature *Zea mays* dihydrodipicolinic acid synthase corresponds to SEQ ID No. 2.

9. A plant which produces free L-lysine by a biosynthetic pathway employing an altered mature *Zea mays* dihydrodipicolinic acid synthase, wherein said altered mature dihydrodipicolinic acid synthase is substantially resistant to feedback inhibition by endogenously produced free L-lysine and is encoded by a recombinant DNA sequence wherein the altered mature dihydrodipicolinic acid synthase has at least one amino acid change in amino acid residues 100 to 125, and said recombinant DNA sequence also expresses a chloroplast transit peptide operably linked to the altered mature dihydrodipicolinic acid synthase.

10. The transformed plant of claim 9 wherein the recombinant DNA sequence corresponds to SEQ ID No. 3.

11. The transformed plant of claim 9 wherein the altered mature *Zea mays* dihydrodipicolinic acid synthase has an amino acid sequence corresponding to SEQ ID No. 2.

12. The transformed plant of claim 9 wherein the plant is a *Zea mays* plant.

13. A chimeric DNA sequence comprising a first DNA sequence which encodes an altered mature *Zea mays* dihydrodipicolinic acid synthase which is substantially resistant to feedback inhibition by L-lysine, and wherein the alteration is at least one amino acid substitution in amino acid residues 100 to 125 of native mature dihydrodipicolinic acid synthase, operably linked to a second DNA sequence attached to the 5'-terminus of the first DNA sequence wherein said second DNA sequence encodes a chloroplast transit peptide and to a promoter functional in a plant cell.

14. The chimeric DNA sequence of claim 13 wherein the first DNA sequence corresponds to SEQ ID No. 1.

15. The chimeric DNA sequence of claim 13 wherein the DNA sequence encodes an altered mature dihydrodipicolinic acid synthase that has an amino acid sequence that corresponds to SEQ ID No. 2.

16. The chimeric DNA sequence of claim 13 wherein the second DNA sequence corresponds to SEQ ID No. 4.

17. The chimeric DNA sequence of claim 13 wherein the amino acid sequence of the chloroplast transit peptide corresponds to SEQ ID No. 5.

18. An isolated, altered, mature *Zea mays* dihydrodipicolinic acid synthase which is substantially resistant to feedback inhibition by L-lysine and wherein the alteration is at least one amino acid substitution in amino acid residues 100 to 125 of native mature dihydrodipicolinic acid synthase.

19. The altered *Zea mays* dihydrodipicolinic acid synthase of claim 18 wherein the alteration is due to about 1–5 amino acid substitutions in the native, mature *Zea mays* dihydrodipicolinic acid synthase amino acid sequence at about amino acid residues 100–125.

20. The altered *Zea mays* dihydrodipicolinic acid synthase of claim 18 wherein the amino acid substitutions are valine or threonine at amino acid residue 112; or lysine at amino acid residue 108.

21. The altered mature *Zea mays* dihydrodipicolinic acid synthase of claim 20 which has an amino acid sequence corresponding to that of SEQ ID No. 2.

22. The altered *Zea mays* dihydrodipicolinic acid synthase of claim 19 wherein the substitution is a lysine at amino acid residue 108.

23. An isolated DNA sequence encoding an altered, mature *Zea mays* dihydrodipicolinic acid synthase which is substantially resistant to feedback inhibition by L-lysine and wherein the alteration is at least one amino acid substitution in amino acid residues 100 to 125 of mature native dihydrodipicolinic acid synthase.

24. The isolated DNA sequence of claim 23 which corresponds to SEQ ID No. 1.

25. A transformed plant according to claim 9 wherein the alteration is at amino acid residue 112.

26. A transformed plant according to claim 9 wherein the alteration is at amino acid residue 108.

27. Seeds of a transformed plant according to claim 9 which comprise said recombinant DNA sequence.

* * * * *

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
    ( A ) LENGTH: 1199 base pairs
    ( B ) TYPE: nucleic acid
    ( C ) STRANDEDNESS: single
    ( D ) TOPOLOGY: linear ( i i ) MOLECULE TYPE: cDNA ( v i i ) IMMEDIATE SOURCE:
    ( B ) CLONE: Mutant DHPS cDNA clone pZM DHPS-M1

( i x ) FEATURE:
    ( A ) NAME/KEY: CDS
    ( B ) LOCATION: 1..981

( x i ) SEQUENCE DESCRIPTION: SEQ ID NO:1:

| GCC | ATC | ACT | CTA | GAT | GAT | TAC | CTT | CCA | ATG | CGA | AGC | ACT | GAA | GTG | AAG | 48 |
| Ala | Ile | Thr | Leu | Asp | Asp | Tyr | Leu | Pro | Met | Arg | Ser | Thr | Glu | Val | Lys | |
| 1 | | | | 5 | | | | | 10 | | | | | 15 | | |

| AAC | CGG | ACA | TCA | ACA | GAT | GAC | ATC | ACA | AGG | CTG | AGA | CTA | ATC | ACA | GCA | 96 |
| Asn | Arg | Thr | Ser | Thr | Asp | Asp | Ile | Thr | Arg | Leu | Arg | Leu | Ile | Thr | Ala | |
| | | | 20 | | | | | 25 | | | | | 30 | | | |

| GTT | AAA | ACC | CCC | TAT | TTG | CCA | GAT | GGG | AGG | TTC | GAT | CTG | GAA | GCA | TAT | 144 |
| Val | Lys | Thr | Pro | Tyr | Leu | Pro | Asp | Gly | Arg | Phe | Asp | Leu | Glu | Ala | Tyr | |
| | | 35 | | | | | 40 | | | | | 45 | | | | |

| GAT | TCT | CTC | ATA | AAC | ATG | CAG | ATA | GAG | GGT | GGT | GCC | GAA | GGC | GTA | ATA | 192 |
| Asp | Ser | Leu | Ile | Asn | Met | Gln | Ile | Glu | Gly | Gly | Ala | Glu | Gly | Val | Ile | |
| | 50 | | | | | 55 | | | | | 60 | | | | | |

| GTT | GGA | GGA | ACA | ACA | GGA | GAG | GGT | CAC | CTC | ATG | AGC | TGG | GAC | GAA | CAT | 240 |
| Val | Gly | Gly | Thr | Thr | Gly | Glu | Gly | His | Leu | Met | Ser | Trp | Asp | Glu | His | |
| 65 | | | | | 70 | | | | | 75 | | | | | 80 | |

| ATC | ATG | CTC | ATT | GGG | CAC | ACA | GTG | AAC | TGC | TTT | GGC | TCT | AGA | ATC | AAA | 288 |
| Ile | Met | Leu | Ile | Gly | His | Thr | Val | Asn | Cys | Phe | Gly | Ser | Arg | Ile | Lys | |
| | | | | 85 | | | | | 90 | | | | | 95 | | |

| GTG | ATA | GGC | AAC | ACA | GGA | AGC | AAC | TCA | ACC | AGA | GAA | GCC | GTC | CAC | GTA | 336 |
| Val | Ile | Gly | Asn | Thr | Gly | Ser | Asn | Ser | Thr | Arg | Glu | Ala | Val | His | Val | |
| | | | 100 | | | | | 105 | | | | | 110 | | | |

| ACA | GAA | CAG | GGA | TTT | GCT | GTT | GGC | ATG | CAT | GCG | GCT | CTC | CAC | ATC | AAT | 384 |
| Thr | Glu | Gln | Gly | Phe | Ala | Val | Gly | Met | His | Ala | Ala | Leu | His | Ile | Asn | |
| | | 115 | | | | | 120 | | | | | 125 | | | | |

| CCT | TAC | TAC | GGG | AAG | ACC | TCA | GCT | GAA | GGA | ATG | ATC | TCT | CAT | TTC | GAG | 432 |
| Pro | Tyr | Tyr | Gly | Lys | Thr | Ser | Ala | Glu | Gly | Met | Ile | Ser | His | Phe | Glu | |
| | 130 | | | | | 135 | | | | | 140 | | | | | |

| GCT | GTC | CTC | CCG | ATG | GGT | CCG | ACC | ATC | ATC | TAC | AAC | GTG | CCA | TCC | AGG | 480 |
| Ala | Val | Leu | Pro | Met | Gly | Pro | Thr | Ile | Ile | Tyr | Asn | Val | Pro | Ser | Arg | |
| 145 | | | | | 150 | | | | | 155 | | | | | 160 | |

| AGC | GCC | CAG | GAC | ATC | CCC | CCT | GAA | GTT | ATT | CTA | GCG | ATT | TCT | GGC | TAC | 528 |
| Ser | Ala | Gln | Asp | Ile | Pro | Pro | Glu | Val | Ile | Leu | Ala | Ile | Ser | Gly | Tyr | |
| | | | | 165 | | | | | 170 | | | | | 175 | | |

| ACA | AAC | ATG | GCG | GGT | GTC | AAG | GAA | TGT | GTT | GGG | CAC | GAG | AGG | GTT | AAG | 576 |
| Thr | Asn | Met | Ala | Gly | Val | Lys | Glu | Cys | Val | Gly | His | Glu | Arg | Val | Lys | |
| | | | 180 | | | | | 185 | | | | | 190 | | | |

```
CAC  TAC  GCT  GAC  AAA  GGC  ATA  ACA  ATT  TGG  AGC  GGT  AAC  GAC  GAC  GAG     624
His  Tyr  Ala  Asp  Lys  Gly  Ile  Thr  Ile  Trp  Ser  Gly  Asn  Asp  Asp  Glu
          195                      200                      205

TGC  CAC  GAT  TCT  AAG  TGG  AAA  CAT  GGC  GCT  ACT  GGG  GTC  ATT  TCC  GTT     672
Cys  His  Asp  Ser  Lys  Trp  Lys  His  Gly  Ala  Thr  Gly  Val  Ile  Ser  Val
     210                           215                      220

ACC  AGC  AAC  CTT  GTT  CCC  GGG  CTC  ATG  CAC  AGC  CTC  ATG  TAC  AAA  GGC     720
Thr  Ser  Asn  Leu  Val  Pro  Gly  Leu  Met  His  Ser  Leu  Met  Tyr  Lys  Gly
225                      230                      235                      240

GAG  AAC  GCC  ACG  CTG  AAC  GAG  AAG  CTG  TCG  CCC  CTG  ATG  AAA  TGG  CTG     768
Glu  Asn  Ala  Thr  Leu  Asn  Glu  Lys  Leu  Ser  Pro  Leu  Met  Lys  Trp  Leu
               245                      250                      255

TTC  TGC  CAG  CCA  AAT  CCT  ATT  GCC  CTC  AAC  ACT  GCT  CTG  GCT  CAG  CTC     816
Phe  Cys  Gln  Pro  Asn  Pro  Ile  Ala  Leu  Asn  Thr  Ala  Leu  Ala  Gln  Leu
               260                      265                      270

GGC  GTG  GCA  AGG  CCT  GTC  TTC  AGA  CTG  CCG  TAC  GTT  CCG  CTC  CCT  CTT     864
Gly  Val  Ala  Arg  Pro  Val  Phe  Arg  Leu  Pro  Tyr  Val  Pro  Leu  Pro  Leu
               275                      280                      285

GAA  AAG  AGG  GCC  GAG  TTC  GTC  CGG  ATT  GTT  GAG  TCA  ATT  GGA  CGG  GAA     912
Glu  Lys  Arg  Ala  Glu  Phe  Val  Arg  Ile  Val  Glu  Ser  Ile  Gly  Arg  Glu
          290                      295                      300

AAT  TTC  GTG  GGG  CAG  AAG  GAG  GCC  CAG  GTT  CTA  GAT  GAT  GAC  GAT  TTC     960
Asn  Phe  Val  Gly  Gln  Lys  Glu  Ala  Gln  Val  Leu  Asp  Asp  Asp  Asp  Phe
305                      310                      315                      320

GTG  TTG  ATC  AGT  AGG  TAC  TAGGAAAATG AGTTTGCTAG TCTATGTATC                     1008
Val  Leu  Ile  Ser  Arg  Tyr
               325

TTGGCGAATA AACTAGTAGT TTGTACCTTG CGTTCAGACT TCGTTCTGTT GTTCATCAGT                  1068

CGTTGGTTTC GTCTATCTAT TTATTAATTG CCTACTTTGG CCGCATTGTA TAATGGATAT                  1128

GTATCGCGTT TATAGTTTTT TACGTGAATT GACCTAGGGA CAAGGAAAAA ATGGTCACTT                  1188

CTTTTTTGGC T                                                                      1199
```

( 2 ) INFORMATION FOR SEQ ID NO:2:

( i ) SEQUENCE CHARACTERISTICS:
        ( A ) LENGTH: 326 amino acids
        ( B ) TYPE: amino acid
        ( D ) TOPOLOGY: linear ( i i ) MOLECULE TYPE: protein ( v i i ) IMMEDIATE SOURCE:
        ( B ) CLONE: Amino Acid Sequence for Maize Mutant DHPS ( x i ) SEQUENCE DESCRIPTION: SEQ ID NO:2:

```
Ala  Ile  Thr  Leu  Asp  Asp  Tyr  Leu  Pro  Met  Arg  Ser  Thr  Glu  Val  Lys
 1             5                      10                      15

Asn  Arg  Thr  Ser  Thr  Asp  Asp  Ile  Thr  Arg  Leu  Arg  Leu  Ile  Thr  Ala
               20                      25                      30

Val  Lys  Thr  Pro  Tyr  Leu  Pro  Asp  Gly  Arg  Phe  Asp  Leu  Glu  Ala  Tyr
               35                      40                      45

Asp  Ser  Leu  Ile  Asn  Met  Gln  Ile  Glu  Gly  Gly  Ala  Glu  Gly  Val  Ile
          50                      55                      60

Val  Gly  Gly  Thr  Thr  Gly  Glu  Gly  His  Leu  Met  Ser  Trp  Asp  Glu  His
65                       70                      75                       80

Ile  Met  Leu  Ile  Gly  His  Thr  Val  Asn  Cys  Phe  Gly  Ser  Arg  Ile  Lys
               85                      90                      95

Val  Ile  Gly  Asn  Thr  Gly  Ser  Asn  Ser  Thr  Arg  Glu  Ala  Val  His  Val
               100                     105                     110
```

```
Thr  Glu  Gln  Gly  Phe  Ala  Val  Gly  Met  His  Ala  Ala  Leu  His  Ile  Asn
          115                 120                      125

Pro  Tyr  Tyr  Gly  Lys  Thr  Ser  Ala  Glu  Gly  Met  Ile  Ser  His  Phe  Glu
     130                 135                      140

Ala  Val  Leu  Pro  Met  Gly  Pro  Thr  Ile  Ile  Tyr  Asn  Val  Pro  Ser  Arg
145                      150                 155                           160

Ser  Ala  Gln  Asp  Ile  Pro  Pro  Glu  Val  Ile  Leu  Ala  Ile  Ser  Gly  Tyr
               165                      170                      175

Thr  Asn  Met  Ala  Gly  Val  Lys  Glu  Cys  Val  Gly  His  Glu  Arg  Val  Lys
               180                 185                      190

His  Tyr  Ala  Asp  Lys  Gly  Ile  Thr  Ile  Trp  Ser  Gly  Asn  Asp  Asp  Glu
          195                 200                      205

Cys  His  Asp  Ser  Lys  Trp  Lys  His  Gly  Ala  Thr  Gly  Val  Ile  Ser  Val
     210                 215                      220

Thr  Ser  Asn  Leu  Val  Pro  Gly  Leu  Met  His  Ser  Leu  Met  Tyr  Lys  Gly
225                      230                 235                           240

Glu  Asn  Ala  Thr  Leu  Asn  Glu  Lys  Leu  Ser  Pro  Leu  Met  Lys  Trp  Leu
               245                      250                      255

Phe  Cys  Gln  Pro  Asn  Pro  Ile  Ala  Leu  Asn  Thr  Ala  Leu  Ala  Gln  Leu
               260                      265                      270

Gly  Val  Ala  Arg  Pro  Val  Phe  Arg  Leu  Pro  Tyr  Val  Pro  Leu  Pro  Leu
          275                      280                      285

Glu  Lys  Arg  Ala  Glu  Phe  Val  Arg  Ile  Val  Glu  Ser  Ile  Gly  Arg  Glu
     290                      295                      300

Asn  Phe  Val  Gly  Gln  Lys  Glu  Ala  Gln  Val  Leu  Asp  Asp  Asp  Asp  Phe
305                      310                      315                      320

Val  Leu  Ile  Ser  Arg  Tyr
                    325
```

( 2 ) INFORMATION FOR SEQ ID NO:3:

( i ) SEQUENCE CHARACTERISTICS:
          ( A ) LENGTH: 1469 base pairs
          ( B ) TYPE: nucleic acid
          ( C ) STRANDEDNESS: single
          ( D ) TOPOLOGY: linear ( i i ) MOLECULE TYPE: cDNA ( v i i ) IMMEDIATE SOURCE:
          ( B ) CLONE: Maize DHPS cDNA Clone pZM DHPS-M1

( i x ) FEATURE:
          ( A ) NAME/KEY: CDS
          ( B ) LOCATION: 109..1251

( x i ) SEQUENCE DESCRIPTION: SEQ ID NO:3:

```
ATGACCATGA  TTACGCCAAG  CTTGCATGCC  TGCAGGTCGA  CTCTAGAGGA  TCCCCGGGTA                60

CCGAGCTCGA  ATTCCACGAC  CACGCCCTCC  GTGCTCCAGC  CATTCCCC  ATG  ATT  TCG         117
                                                          Met  Ile  Ser
                                                            1

CCG  ACG  AAT  CTC  CTC  CCG  GCG  CGG  AAG  ATC  ACC  CCT  GTC  TCA  AAT  GGC   165
Pro  Thr  Asn  Leu  Leu  Pro  Ala  Arg  Lys  Ile  Thr  Pro  Val  Ser  Asn  Gly
       5                   10                      15

GGC  GCA  GCG  ACG  GCG  AGC  CCC  TCT  TCT  CCC  TCG  GTG  GCC  GCA  CGG  CCA   213
Gly  Ala  Ala  Thr  Ala  Ser  Pro  Ser  Ser  Pro  Ser  Val  Ala  Ala  Arg  Pro
 20                  25                      30                           35

CGG  CGA  CTC  CCT  TCA  GGC  CTC  CAA  TCT  GTG  ACT  GGT  AGA  GGG  AAG  GTT   261
Arg  Arg  Leu  Pro  Ser  Gly  Leu  Gln  Ser  Val  Thr  Gly  Arg  Gly  Lys  Val
                    40                      45                           50
```

| | | | | | | | | | | | | | | | | |
|---|---|---|---|---|---|---|---|---|---|---|---|---|---|---|---|---|
| TCC | TTG | GCA | GCC | ATC | ACT | CTA | GAT | GAT | TAC | CTT | CCA | ATG | CGA | AGC | ACT | 309 |
| Ser | Leu | Ala | Ala | Ile | Thr | Leu | Asp | Asp | Tyr | Leu | Pro | Met | Arg | Ser | Thr | |
| | | | 55 | | | | 60 | | | | | | 65 | | | |
| GAA | GTG | AAG | AAC | CGG | ACA | TCA | ACA | GAT | GAC | ATC | ACA | AGG | CTG | AGA | CTA | 357 |
| Glu | Val | Lys | Asn | Arg | Thr | Ser | Thr | Asp | Asp | Ile | Thr | Arg | Leu | Arg | Leu | |
| | | 70 | | | | 75 | | | | | 80 | | | | | |
| ATC | ACA | GCA | GTT | AAA | ACC | CCC | TAT | TTG | CCA | GAT | GGG | AGG | TTC | GAT | CTG | 405 |
| Ile | Thr | Ala | Val | Lys | Thr | Pro | Tyr | Leu | Pro | Asp | Gly | Arg | Phe | Asp | Leu | |
| | 85 | | | | | 90 | | | | | 95 | | | | | |
| GAA | GCA | TAT | GAT | TCT | CTC | ATA | AAC | ATG | CAG | ATA | GAG | GGT | GGT | GCC | GAA | 453 |
| Glu | Ala | Tyr | Asp | Ser | Leu | Ile | Asn | Met | Gln | Ile | Glu | Gly | Gly | Ala | Glu | |
| 100 | | | | | 105 | | | | | 110 | | | | | 115 | |
| GGC | GTA | ATA | GTT | GGA | GGA | ACA | ACA | GGA | GAG | GGT | CAC | CTC | ATG | AGC | TGG | 501 |
| Gly | Val | Ile | Val | Gly | Gly | Thr | Thr | Gly | Glu | Gly | His | Leu | Met | Ser | Trp | |
| | | | 120 | | | | | 125 | | | | | 130 | | | |
| GAC | GAA | CAT | ATC | ATG | CTC | ATT | GGG | CAC | ACA | GTG | AAC | TGC | TTT | GGC | TCT | 549 |
| Asp | Glu | His | Ile | Met | Leu | Ile | Gly | His | Thr | Val | Asn | Cys | Phe | Gly | Ser | |
| | | | 135 | | | | | 140 | | | | | 145 | | | |
| AGA | ATC | AAA | GTG | ATA | GGC | AAC | ACA | GGA | AGC | AAC | TCA | ACC | AGA | GAA | GCC | 597 |
| Arg | Ile | Lys | Val | Ile | Gly | Asn | Thr | Gly | Ser | Asn | Ser | Thr | Arg | Glu | Ala | |
| | | 150 | | | | | 155 | | | | | 160 | | | | |
| GTC | CAC | GTA | ACA | GAA | CAG | GGA | TTT | GCT | GTT | GGC | ATG | CAT | GCG | GCT | CTC | 645 |
| Val | His | Val | Thr | Glu | Gln | Gly | Phe | Ala | Val | Gly | Met | His | Ala | Ala | Leu | |
| | 165 | | | | | 170 | | | | | 175 | | | | | |
| CAC | ATC | AAT | CCT | TAC | TAC | GGG | AAG | ACC | TCA | GCT | GAA | GGA | ATG | ATC | TCT | 693 |
| His | Ile | Asn | Pro | Tyr | Tyr | Gly | Lys | Thr | Ser | Ala | Glu | Gly | Met | Ile | Ser | |
| 180 | | | | | 185 | | | | | 190 | | | | | 195 | |
| CAT | TTC | GAG | GCT | GTC | CTC | CCG | ATG | GGT | CCG | ACC | ATC | ATC | TAC | AAC | GTG | 741 |
| His | Phe | Glu | Ala | Val | Leu | Pro | Met | Gly | Pro | Thr | Ile | Ile | Tyr | Asn | Val | |
| | | | | 200 | | | | | 205 | | | | | 210 | | |
| CCA | TCC | AGG | AGC | GCC | CAG | GAC | ATC | CCC | CCT | GAA | GTT | ATT | CTA | GCG | ATT | 789 |
| Pro | Ser | Arg | Ser | Ala | Gln | Asp | Ile | Pro | Pro | Glu | Val | Ile | Leu | Ala | Ile | |
| | | | 215 | | | | | 220 | | | | | 225 | | | |
| TCT | GGC | TAC | ACA | AAC | ATG | GCG | GGT | GTC | AAG | GAA | TGT | GTT | GGG | CAC | GAG | 837 |
| Ser | Gly | Tyr | Thr | Asn | Met | Ala | Gly | Val | Lys | Glu | Cys | Val | Gly | His | Glu | |
| | | 230 | | | | | 235 | | | | | 240 | | | | |
| AGG | GTT | AAG | CAC | TAC | GCT | GAC | AAA | GGC | ATA | ACA | ATT | TGG | AGC | GGT | AAC | 885 |
| Arg | Val | Lys | His | Tyr | Ala | Asp | Lys | Gly | Ile | Thr | Ile | Trp | Ser | Gly | Asn | |
| | 245 | | | | | 250 | | | | | 255 | | | | | |
| GAC | GAC | GAG | TGC | CAC | GAT | TCT | AAG | TGG | AAA | CAT | GGC | GCT | ACT | GGG | GTC | 933 |
| Asp | Asp | Glu | Cys | His | Asp | Ser | Lys | Trp | Lys | His | Gly | Ala | Thr | Gly | Val | |
| 260 | | | | | 265 | | | | | 270 | | | | | 275 | |
| ATT | TCC | GTT | ACC | AGC | AAC | CTT | GTT | CCC | GGG | CTC | ATG | CAC | AGC | CTC | ATG | 981 |
| Ile | Ser | Val | Thr | Ser | Asn | Leu | Val | Pro | Gly | Leu | Met | His | Ser | Leu | Met | |
| | | | | 280 | | | | | 285 | | | | | 290 | | |
| TAC | AAA | GGC | GAG | AAC | GCC | ACG | CTG | AAC | GAG | AAG | CTG | TCG | CCC | CTG | ATG | 1029 |
| Tyr | Lys | Gly | Glu | Asn | Ala | Thr | Leu | Asn | Glu | Lys | Leu | Ser | Pro | Leu | Met | |
| | | | 295 | | | | | 300 | | | | | 305 | | | |
| AAA | TGG | CTG | TTC | TGC | CAG | CCA | AAT | CCT | ATT | GCC | CTC | AAC | ACT | GCT | CTG | 1077 |
| Lys | Trp | Leu | Phe | Cys | Gln | Pro | Asn | Pro | Ile | Ala | Leu | Asn | Thr | Ala | Leu | |
| | | 310 | | | | | 315 | | | | | 320 | | | | |
| GCT | CAG | CTC | GGC | GTG | GCA | AGG | CCT | GTC | TTC | AGA | CTG | CCG | TAC | GTT | CCG | 1125 |
| Ala | Gln | Leu | Gly | Val | Ala | Arg | Pro | Val | Phe | Arg | Leu | Pro | Tyr | Val | Pro | |
| | 325 | | | | | 330 | | | | | 335 | | | | | |
| CTC | CCT | CTT | GAA | AAG | AGG | GCC | GAG | TTC | GTC | CGG | ATT | GTT | GAG | TCA | ATT | 1173 |
| Leu | Pro | Leu | Glu | Lys | Arg | Ala | Glu | Phe | Val | Arg | Ile | Val | Glu | Ser | Ile | |
| 340 | | | | | 345 | | | | | 350 | | | | | 355 | |
| GGA | CGG | GAA | AAT | TTC | GTG | GGG | CAG | AAG | GAG | GCC | CAG | GTT | CTA | GAT | GAT | 1221 |
| Gly | Arg | Glu | Asn | Phe | Val | Gly | Gln | Lys | Glu | Ala | Gln | Val | Leu | Asp | Asp | |
| | | | | 360 | | | | | 365 | | | | | 370 | | |

```
GAC GAT TTC GTG TTG ATC AGT AGG TAC TAGGAAAATG AGTTTGCTAG                       1268
Asp Asp Phe Val Leu Ile Ser Arg Tyr
            375                 380

TCTATGTATC TTGGCGAATA AACTAGTAGT TTGTACCTTG CGTTCAGACT TCGTTCTGTT               1328

GTTCATCAGT CGTTGGTTTC GTCTATCTAT TTATTAATTG CCTACTTTGG CCGCATTGTA               1388

TAATGGATAT GTATCGCGTT TATAGTTTTT TACGTGAATT GACCTAGGGA CAAGGAAAAA               1448

ATGGTCACTT CTTTTTTGGC T                                                         1469
```

( 2 ) INFORMATION FOR SEQ ID NO:4:

( i ) SEQUENCE CHARACTERISTICS:
        ( A ) LENGTH: 162 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: Maize chloroplast transit peptide ( i x ) FEATURE:
        ( A ) NAME/KEY: CDS
        ( B ) LOCATION: 1..162

( x i ) SEQUENCE DESCRIPTION: SEQ ID NO:4:

```
ATG ATT TCG CCG ACG AAT CTC CTC CCG GCG CGG AAG ATC ACC CCT GTC               48
Met Ile Ser Pro Thr Asn Leu Leu Pro Ala Arg Lys Ile Thr Pro Val
 1               5                  10                  15

TCA AAT GGC GGC GCA GCG ACG GCG AGC CCC TCT TCT CCC TCG GTG GCC               96
Ser Asn Gly Gly Ala Ala Thr Ala Ser Pro Ser Ser Pro Ser Val Ala
            20                  25                  30

GCA CGG CCA CGG CGA CTC CCT TCA GGC CTC CAA TCT GTG ACT GGT AGA              144
Ala Arg Pro Arg Arg Leu Pro Ser Gly Leu Gln Ser Val Thr Gly Arg
        35                  40                  45

GGG AAG GTT TCC TTG GCA                                                      162
Gly Lys Val Ser Leu Ala
 50
```

( 2 ) INFORMATION FOR SEQ ID NO:5:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: protein ( v i i ) IMMEDIATE SOURCE:
        ( B ) CLONE: Amino acid chloroplast transit peptide ( x i ) SEQUENCE DESCRIPTION: SEQ ID NO:5:

```
Met Ile Ser Pro Thr Asn Leu Leu Pro Ala Arg Lys Ile Thr Pro Val
 1               5                  10                  15

Ser Asn Gly Gly Ala Ala Thr Ala Ser Pro Ser Ser Pro Ser Val Ala
            20                  25                  30

Ala Arg Pro Arg Arg Leu Pro Ser Gly Leu Gln Ser Val Thr Gly Arg
        35                  40                  45

Gly Lys Val Ser Leu Ala
 50
```

( 2 ) INFORMATION FOR SEQ ID NO:6:

( i ) SEQUENCE CHARACTERISTICS:
        ( A ) LENGTH: 1469 base pairs ( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( B ) CLONE: Maize DHPS cDNA Clone pZM DHPS5B ( i x ) FEATURE:
( A ) NAME/KEY: CDS
( B ) LOCATION: 109..1251

( x i ) SEQUENCE DESCRIPTION: SEQ ID NO:6:

```
ATGACCATGA TTACGCCAAG CTTGCATGCC TGCAGGTCGA CTCTAGAGGA TCCCCGGGTA            60

CCGAGCTCGA ATTCCACGAC CACGCCCTCC GTGCTCCAGC CATTCCCC ATG ATT TCG           117
                                                     Met Ile Ser
                                                       1

CCG ACG AAT CTC CTC CCG GCG CGG AAG ATC ACC CCT GTC TCA AAT GGC           165
Pro Thr Asn Leu Leu Pro Ala Arg Lys Ile Thr Pro Val Ser Asn Gly
      5               10                  15

GGC GCA GCG ACG GCG AGC CCC TCT TCT CCC TCG GTG GCC GCA CGG CCA           213
Gly Ala Ala Thr Ala Ser Pro Ser Ser Pro Ser Val Ala Ala Arg Pro
 20              25                  30                      35

CGG CGA CTC CCT TCA GGC CTC CAA TCT GTG ACT GGT AGA GGG AAG GTT           261
Arg Arg Leu Pro Ser Gly Leu Gln Ser Val Thr Gly Arg Gly Lys Val
              40                  45                  50

TCC TTG GCA GCC ATC ACT CTA GAT GAT TAC CTT CCA ATG CGA AGC ACT           309
Ser Leu Ala Ala Ile Thr Leu Asp Asp Tyr Leu Pro Met Arg Ser Thr
          55                  60                  65

GAA GTG AAG AAC CGG ACA TCA ACA GAT GAC ATC ACA AGG CTG AGA CTA           357
Glu Val Lys Asn Arg Thr Ser Thr Asp Asp Ile Thr Arg Leu Arg Leu
      70                  75                  80

ATC ACA GCA GTT AAA ACC CCC TAT TTG CCA GAT GGG AGG TTC GAT CTG           405
Ile Thr Ala Val Lys Thr Pro Tyr Leu Pro Asp Gly Arg Phe Asp Leu
  85                  90                  95

GAA GCA TAT GAT TCT CTC ATA AAC ATG CAG ATA GAG GGT GGT GCC GAA           453
Glu Ala Tyr Asp Ser Leu Ile Asn Met Gln Ile Glu Gly Gly Ala Glu
100              105                 110                     115

GGC GTA ATA GTT GGA GGA ACA ACA GGA GAG GGT CAC CTC ATG AGC TGG           501
Gly Val Ile Val Gly Gly Thr Thr Gly Glu Gly His Leu Met Ser Trp
              120                 125                 130

GAC GAA CAT ATC ATG CTC ATT GGG CAC ACA GTG AAC TGC TTT GGC TCT           549
Asp Glu His Ile Met Leu Ile Gly His Thr Val Asn Cys Phe Gly Ser
          135                 140                 145

AGA ATC AAA GTG ATA GGC AAC ACA GGA AGC AAC TCA ACC AGA GAA GCC           597
Arg Ile Lys Val Ile Gly Asn Thr Gly Ser Asn Ser Thr Arg Glu Ala
         150                  155                 160

GTC CAC GCA ACA GAA CAG GGA TTT GCT GTT GGC ATG CAT GCG GCT CTC           645
Val His Ala Thr Glu Gln Gly Phe Ala Val Gly Met His Ala Ala Leu
    165                 170                 175

CAC ATC AAT CCT TAC TAC GGG AAG ACC TCA GCT GAA GGA ATG ATC TCT           693
His Ile Asn Pro Tyr Tyr Gly Lys Thr Ser Ala Glu Gly Met Ile Ser
180                 185                 190                 195

CAT TTC GAG GCT GTC CTC CCG ATG GGT CCG ACC ATC ATC TAC AAC GTG           741
His Phe Glu Ala Val Leu Pro Met Gly Pro Thr Ile Ile Tyr Asn Val
              200                 205                 210

CCA TCC AGG AGC GCC CAG GAC ATC CCC CCT GAA GTT ATT CTA GCG ATT           789
Pro Ser Arg Ser Ala Gln Asp Ile Pro Pro Glu Val Ile Leu Ala Ile
          215                 220                 225

TCT GGC TAC ACA AAC ATG GCG GGT GTC AAG GAA TGT GTT GGG CAC GAG           837
Ser Gly Tyr Thr Asn Met Ala Gly Val Lys Glu Cys Val Gly His Glu
         230                  235                     240
```

```
AGG GTT AAG CAC TAC GCT GAC AAA GGC ATA ACA ATT TGG AGC GGT AAC        885
Arg Val Lys His Tyr Ala Asp Lys Gly Ile Thr Ile Trp Ser Gly Asn
    245             250                 255

GAC GAC GAG TGC CAC GAT TCT AAG TGG AAA CAT GGC GCT ACT GGG GTC        933
Asp Asp Glu Cys His Asp Ser Lys Trp Lys His Gly Ala Thr Gly Val
260             265                 270                 275

ATT TCC GTT ACC AGC AAC CTT GTT CCC GGG CTC ATG CAC AGC CTC ATG        981
Ile Ser Val Thr Ser Asn Leu Val Pro Gly Leu Met His Ser Leu Met
                280                 285                 290

TAC AAA GGC GAG AAC GCC ACG CTG AAC GAG AAG CTG TCG CCC CTG ATG       1029
Tyr Lys Gly Glu Asn Ala Thr Leu Asn Glu Lys Leu Ser Pro Leu Met
            295                 300                 305

AAA TGG CTG TTC TGC CAG CCA AAT CCT ATT GCC CTC AAC ACT GCT CTG       1077
Lys Trp Leu Phe Cys Gln Pro Asn Pro Ile Ala Leu Asn Thr Ala Leu
        310                 315                 320

GCT CAG CTC GGC GTG GCA AGG CCT GTC TTC AGA CTG CCG TAC GTT CCG       1125
Ala Gln Leu Gly Val Ala Arg Pro Val Phe Arg Leu Pro Tyr Val Pro
    325                 330                 335

CTC CCT CTT GAA AAG AGG GCC GAG TTC GTC CGG ATT GTT GAG TCA ATT       1173
Leu Pro Leu Glu Lys Arg Ala Glu Phe Val Arg Ile Val Glu Ser Ile
340                 345                 350                 355

GGA CGG GAA AAT TTC GTG GGG CAG AAG GAG GCC CAG GTT CTA GAT GAT       1221
Gly Arg Glu Asn Phe Val Gly Gln Lys Glu Ala Gln Val Leu Asp Asp
                360                 365                 370

GAC GAT TTC GTG TTG ATC AGT AGG TAC TAGGAAAATG AGTTTGCTAG             1268
Asp Asp Phe Val Leu Ile Ser Arg Tyr
                375             380

TCTATGTATC TTGGCGAATA AACTAGTAGT TTGTACCTTG CGTTCAGACT TCGTTCTGTT     1328

GTTCATCAGT CGTTGGTTTC GTCTATCTAT TTATTAATTG CCTACTTTGG CCGCATTGTA     1388

TAATGGATAT GTATCGCGTT TATAGTTTTT TACGTGAATT GACCTAGGGA CAAGGAAAAA     1448

ATGGTCACTT CTTTTTTGGC T                                               1469

( 2 ) INFORMATION FOR SEQ ID NO:7:

( i ) SEQUENCE CHARACTERISTICS:
                ( A ) LENGTH: 1199 base pairs
                ( B ) TYPE: nucleic acid
                ( C ) STRANDEDNESS: single
                ( D ) TOPOLOGY: linear ( i i ) MOLECULE TYPE: cDNA ( v i i ) IMMEDIATE SOURCE:
                ( B ) CLONE: Maize DHPS cDNA clone pZM DHPS5B ( i x ) FEATURE:
                ( A ) NAME/KEY: CDS
                ( B ) LOCATION: 1..981

( x i ) SEQUENCE DESCRIPTION: SEQ ID NO:7:

GCC ATC ACT CTA GAT GAT TAC CTT CCA ATG CGA AGC ACT GAA GTG AAG         48
Ala Ile Thr Leu Asp Asp Tyr Leu Pro Met Arg Ser Thr Glu Val Lys
1               5                   10                  15

AAC CGG ACA TCA ACA GAT GAC ATC ACA AGG CTG AGA CTA ATC ACA GCA         96
Asn Arg Thr Ser Thr Asp Asp Ile Thr Arg Leu Arg Leu Ile Thr Ala
                20                  25                  30

GTT AAA ACC CCC TAT TTG CCA GAT GGG AGG TTC GAT CTG GAA GCA TAT        144
Val Lys Thr Pro Tyr Leu Pro Asp Gly Arg Phe Asp Leu Glu Ala Tyr
            35                  40                  45

GAT TCT CTC ATA AAC ATG CAG ATA GAG GGT GGT GCC GAA GGC GTA ATA        192
Asp Ser Leu Ile Asn Met Gln Ile Glu Gly Gly Ala Glu Gly Val Ile
        50                  55                  60
```

| | | | | | | | | | | | | | | | | |
|---|---|---|---|---|---|---|---|---|---|---|---|---|---|---|---|---|
| GTT | GGA | GGA | ACA | ACA | GGA | GAG | GGT | CAC | CTC | ATG | AGC | TGG | GAC | GAA | CAT | 240 |
| Val | Gly | Gly | Thr | Thr | Gly | Glu | Gly | His | Leu | Met | Ser | Trp | Asp | Glu | His | |
| 65 | | | | 70 | | | | 75 | | | | | | | 80 | |
| ATC | ATG | CTC | ATT | GGG | CAC | ACA | GTG | AAC | TGC | TTT | GGC | TCT | AGA | ATC | AAA | 288 |
| Ile | Met | Leu | Ile | Gly | His | Thr | Val | Asn | Cys | Phe | Gly | Ser | Arg | Ile | Lys | |
| | | | | 85 | | | | 90 | | | | | 95 | | | |
| GTG | ATA | GGC | AAC | ACA | GGA | AGC | AAC | TCA | ACC | AGA | GAA | GCC | GTC | CAC | GCA | 336 |
| Val | Ile | Gly | Asn | Thr | Gly | Ser | Asn | Ser | Thr | Arg | Glu | Ala | Val | His | Ala | |
| | | | 100 | | | | 105 | | | | | 110 | | | | |
| ACA | GAA | CAG | GGA | TTT | GCT | GTT | GGC | ATG | CAT | GCG | GCT | CTC | CAC | ATC | AAT | 384 |
| Thr | Glu | Gln | Gly | Phe | Ala | Val | Gly | Met | His | Ala | Ala | Leu | His | Ile | Asn | |
| | | 115 | | | | 120 | | | | | 125 | | | | | |
| CCT | TAC | TAC | GGG | AAG | ACC | TCA | GCT | GAA | GGA | ATG | ATC | TCT | CAT | TTC | GAG | 432 |
| Pro | Tyr | Tyr | Gly | Lys | Thr | Ser | Ala | Glu | Gly | Met | Ile | Ser | His | Phe | Glu | |
| | 130 | | | | 135 | | | | | 140 | | | | | | |
| GCT | GTC | CTC | CCG | ATG | GGT | CCG | ACC | ATC | ATC | TAC | AAC | GTG | CCA | TCC | AGG | 480 |
| Ala | Val | Leu | Pro | Met | Gly | Pro | Thr | Ile | Ile | Tyr | Asn | Val | Pro | Ser | Arg | |
| 145 | | | | 150 | | | | 155 | | | | | 160 | | | |
| AGC | GCC | CAG | GAC | ATC | CCC | CCT | GAA | GTT | ATT | CTA | GCG | ATT | TCT | GGC | TAC | 528 |
| Ser | Ala | Gln | Asp | Ile | Pro | Pro | Glu | Val | Ile | Leu | Ala | Ile | Ser | Gly | Tyr | |
| | | | 165 | | | | 170 | | | | | 175 | | | | |
| ACA | AAC | ATG | GCG | GGT | GTC | AAG | GAA | TGT | GTT | GGG | CAC | GAG | AGG | GTT | AAG | 576 |
| Thr | Asn | Met | Ala | Gly | Val | Lys | Glu | Cys | Val | Gly | His | Glu | Arg | Val | Lys | |
| | | | 180 | | | | 185 | | | | | 190 | | | | |
| CAC | TAC | GCT | GAC | AAA | GGC | ATA | ACA | ATT | TGG | AGC | GGT | AAC | GAC | GAC | GAG | 624 |
| His | Tyr | Ala | Asp | Lys | Gly | Ile | Thr | Ile | Trp | Ser | Gly | Asn | Asp | Asp | Glu | |
| | | 195 | | | | 200 | | | | | 205 | | | | | |
| TGC | CAC | GAT | TCT | AAG | TGG | AAA | CAT | GGC | GCT | ACT | GGG | GTC | ATT | TCC | GTT | 672 |
| Cys | His | Asp | Ser | Lys | Trp | Lys | His | Gly | Ala | Thr | Gly | Val | Ile | Ser | Val | |
| | 210 | | | | 215 | | | | | 220 | | | | | | |
| ACC | AGC | AAC | CTT | GTT | CCC | GGG | CTC | ATG | CAC | AGC | CTC | ATG | TAC | AAA | GGC | 720 |
| Thr | Ser | Asn | Leu | Val | Pro | Gly | Leu | Met | His | Ser | Leu | Met | Tyr | Lys | Gly | |
| 225 | | | | 230 | | | | 235 | | | | | 240 | | | |
| GAG | AAC | GCC | ACG | CTG | AAC | GAG | AAG | CTG | TCG | CCC | CTG | ATG | AAA | TGG | CTG | 768 |
| Glu | Asn | Ala | Thr | Leu | Asn | Glu | Lys | Leu | Ser | Pro | Leu | Met | Lys | Trp | Leu | |
| | | | | 245 | | | | 250 | | | | | 255 | | | |
| TTC | TGC | CAG | CCA | AAT | CCT | ATT | GCC | CTC | AAC | ACT | GCT | CTG | GCT | CAG | CTC | 816 |
| Phe | Cys | Gln | Pro | Asn | Pro | Ile | Ala | Leu | Asn | Thr | Ala | Leu | Ala | Gln | Leu | |
| | | | 260 | | | | 265 | | | | | 270 | | | | |
| GGC | GTG | GCA | AGG | CCT | GTC | TTC | AGA | CTG | CCG | TAC | GTT | CCG | CTC | CCT | CTT | 864 |
| Gly | Val | Ala | Arg | Pro | Val | Phe | Arg | Leu | Pro | Tyr | Val | Pro | Leu | Pro | Leu | |
| | | 275 | | | | 280 | | | | | 285 | | | | | |
| GAA | AAG | AGG | GCC | GAG | TTC | GTC | CGG | ATT | GTT | GAG | TCA | ATT | GGA | CGG | GAA | 912 |
| Glu | Lys | Arg | Ala | Glu | Phe | Val | Arg | Ile | Val | Glu | Ser | Ile | Gly | Arg | Glu | |
| | 290 | | | | 295 | | | | | 300 | | | | | | |
| AAT | TTC | GTG | GGG | CAG | AAG | GAG | GCC | CAG | GTT | CTA | GAT | GAT | GAC | GAT | TTC | 960 |
| Asn | Phe | Val | Gly | Gln | Lys | Glu | Ala | Gln | Val | Leu | Asp | Asp | Asp | Asp | Phe | |
| 305 | | | | 310 | | | | 315 | | | | | 320 | | | |
| GTG | TTG | ATC | AGT | AGG | TAC | TAGGAAAATG | AGTTGCTAG | TCTATGTATC | | | | | | | | 1008 |
| Val | Leu | Ile | Ser | Arg | Tyr | | | | | | | | | | | |
| | | | | 325 | | | | | | | | | | | | |

```
TTGGCGAATA AACTAGTAGT TTGTACCTTG CGTTCAGACT TCGTTCTGTT GTTCATCAGT      1068

CGTTGGTTTC GTCTATCTAT TTATTAATTG CCTACTTTGG CCGCATTGTA TAATGGATAT      1128

GTATCGCGTT TATAGTTTTT TACGTGAATT GACCTAGGGA CAAGGAAAAA ATGGTCACTT      1188

CTTTTTTGGC T                                                           1199
```

( 2 ) INFORMATION FOR SEQ ID NO:8:

( i ) SEQUENCE CHARACTERISTICS:
  ( A ) LENGTH: 326 amino acids
  ( B ) TYPE: amino acid
  ( D ) TOPOLOGY: linear ( i i ) MOLECULE TYPE: protein ( x i ) SEQUENCE DESCRIPTION: SEQ ID NO:8:

| Ala | Ile | Thr | Leu | Asp | Asp | Tyr | Leu | Pro | Met | Arg | Ser | Thr | Glu | Val | Lys |
|---|---|---|---|---|---|---|---|---|---|---|---|---|---|---|---|
| 1 | | | | 5 | | | | | 10 | | | | | 15 | |
| Asn | Arg | Thr | Ser | Thr | Asp | Asp | Ile | Thr | Arg | Leu | Arg | Leu | Ile | Thr | Ala |
| | | | 20 | | | | | 25 | | | | | 30 | | |
| Val | Lys | Thr | Pro | Tyr | Leu | Pro | Asp | Gly | Arg | Phe | Asp | Leu | Glu | Ala | Tyr |
| | | 35 | | | | | 40 | | | | | 45 | | | |
| Asp | Ser | Leu | Ile | Asn | Met | Gln | Ile | Glu | Gly | Gly | Ala | Glu | Gly | Val | Ile |
| | 50 | | | | | 55 | | | | | 60 | | | | |
| Val | Gly | Gly | Thr | Thr | Gly | Glu | Gly | His | Leu | Met | Ser | Trp | Asp | Glu | His |
| 65 | | | | | 70 | | | | | 75 | | | | | 80 |
| Ile | Met | Leu | Ile | Gly | His | Thr | Val | Asn | Cys | Phe | Gly | Ser | Arg | Ile | Lys |
| | | | | 85 | | | | | 90 | | | | | 95 | |
| Val | Ile | Gly | Asn | Thr | Gly | Ser | Asn | Ser | Thr | Arg | Glu | Ala | Val | His | Ala |
| | | | 100 | | | | | 105 | | | | | 110 | | |
| Thr | Glu | Gln | Gly | Phe | Ala | Val | Gly | Met | His | Ala | Ala | Leu | His | Ile | Asn |
| | | 115 | | | | | 120 | | | | | 125 | | | |
| Pro | Tyr | Tyr | Gly | Lys | Thr | Ser | Ala | Glu | Gly | Met | Ile | Ser | His | Phe | Glu |
| | 130 | | | | | 135 | | | | | 140 | | | | |
| Ala | Val | Leu | Pro | Met | Gly | Pro | Thr | Ile | Ile | Tyr | Asn | Val | Pro | Ser | Arg |
| 145 | | | | | 150 | | | | | 155 | | | | | 160 |
| Ser | Ala | Gln | Asp | Ile | Pro | Pro | Glu | Val | Ile | Leu | Ala | Ile | Ser | Gly | Tyr |
| | | | | 165 | | | | | 170 | | | | | 175 | |
| Thr | Asn | Met | Ala | Gly | Val | Lys | Glu | Cys | Val | Gly | His | Glu | Arg | Val | Lys |
| | | | 180 | | | | | 185 | | | | | 190 | | |
| His | Tyr | Ala | Asp | Lys | Gly | Ile | Thr | Ile | Trp | Ser | Gly | Asn | Asp | Asp | Glu |
| | | 195 | | | | | 200 | | | | | 205 | | | |
| Cys | His | Asp | Ser | Lys | Trp | Lys | His | Gly | Ala | Thr | Gly | Val | Ile | Ser | Val |
| | 210 | | | | | 215 | | | | | 220 | | | | |
| Thr | Ser | Asn | Leu | Val | Pro | Gly | Leu | Met | His | Ser | Leu | Met | Tyr | Lys | Gly |
| 225 | | | | | 230 | | | | | 235 | | | | | 240 |
| Glu | Asn | Ala | Thr | Leu | Asn | Glu | Lys | Leu | Ser | Pro | Leu | Met | Lys | Trp | Leu |
| | | | | 245 | | | | | 250 | | | | | 255 | |
| Phe | Cys | Gln | Pro | Asn | Pro | Ile | Ala | Leu | Asn | Thr | Ala | Leu | Ala | Gln | Leu |
| | | | 260 | | | | | 265 | | | | | 270 | | |
| Gly | Val | Ala | Arg | Pro | Val | Phe | Arg | Leu | Pro | Tyr | Val | Pro | Leu | Pro | Leu |
| | | 275 | | | | | 280 | | | | | 285 | | | |
| Glu | Lys | Arg | Ala | Glu | Phe | Val | Arg | Ile | Val | Glu | Ser | Ile | Gly | Arg | Glu |
| | 290 | | | | | 295 | | | | | 300 | | | | |
| Asn | Phe | Val | Gly | Gln | Lys | Glu | Ala | Gln | Val | Leu | Asp | Asp | Asp | Asp | Phe |
| 305 | | | | | 310 | | | | | 315 | | | | | 320 |
| Val | Leu | Ile | Ser | Arg | Tyr | | | | | | | | | | |
| | | | | 325 | | | | | | | | | | | |

( 2 ) INFORMATION FOR SEQ ID NO:9:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:9:

CGACTCCCTT CAGGCCTC　　　　　　　　　　　　　　　　　　　　　　　　　　18

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GATTCTCTCA TAAACATG　　　　　　　　　　　　　　　　　　　　　　　　　　18

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

ACCAGAGAAG CCGTCCACGC AACAGAA　　　　　　　　　　　　　　　　　　　27

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

AACATGGCGG GTGTCAAGGA A　　　　　　　　　　　　　　　　　　　　　　21

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

AAGCTGTCGC CCCTGATG　　　　　　　　　　　　　　　　　　　　　　　　　18

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

TGGCAAATAG GGGGTTTTAA C                                               21

( 2 ) INFORMATION FOR SEQ ID NO:15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GCTTCCTGTG TTGCCTATCA C                                               21

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

AGAAATCGCT AGAATAACTT C                                               21

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

CTCGCCTTTG TACATGAGGC T                                               21

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

TAGAACCTGG GCCTCCTTCT G                                               21

( 2 ) INFORMATION FOR SEQ ID NO:19:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

CGCGGGATCC ATGATTTCGC CGACGAATCT CC                                   32

( 2 ) INFORMATION FOR SEQ ID NO:20:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:20:

ACAACTAGTC ATCCATGATC CTTAAGTAGC    30

( 2 ) INFORMATION FOR SEQ ID NO:21:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:21:

CGCGGGATCC ATGATTTCGC CGACGAATCT CC    32

( 2 ) INFORMATION FOR SEQ ID NO:22:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:22:

GCACAACTAG TCATCCATGA TCCTCGAGGC GC    32